(12) United States Patent
Labella et al.

(10) Patent No.: US 12,360,262 B2
(45) Date of Patent: Jul. 15, 2025

(54) SYSTEM AND METHOD FOR POWER-EFFICIENT MULTIPLEXING FOR HIGH RESOLUTION TIME-OF-FLIGHT POSITRON EMISSION TOMOGRAPHY MODULES WITH INTERCRYSTAL LIGHT SHARING

(71) Applicant: THE RESEARCH FOUNDATION FOR THE STATE UNIVERSITY OF NEW YORK, Albany, NY (US)

(72) Inventors: Andrew Labella, Stony Brook, NY (US); Amirhossein Goldan, Stony Brook, NY (US); Eric Petersen, Stony Brook, NY (US); Wei Zhao, Stony Brook, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 286 days.

(21) Appl. No.: 18/030,851

(22) PCT Filed: Oct. 7, 2021

(86) PCT No.: PCT/US2021/053896
§ 371 (c)(1),
(2) Date: Apr. 7, 2023

(87) PCT Pub. No.: WO2022/076643
PCT Pub. Date: Apr. 14, 2022

(65) Prior Publication Data
US 2023/0375731 A1 Nov. 23, 2023

Related U.S. Application Data

(60) Provisional application No. 63/088,718, filed on Oct. 7, 2020, provisional application No. 63/110,109, filed on Nov. 5, 2020.

(51) Int. Cl.
*G01T 1/29* (2006.01)
*A61B 6/03* (2006.01)
(Continued)

(52) U.S. Cl.
CPC ............ *G01T 1/2985* (2013.01); *A61B 6/037* (2013.01); *A61B 6/4258* (2013.01); *G06T 11/005* (2013.01); *G06T 2207/10104* (2013.01)

(58) Field of Classification Search
CPC ... G01T 1/2985; G01T 1/1642; G01T 1/2002; A61B 6/037; A61B 6/4258; G06T 11/005
See application file for complete search history.

(56) References Cited

U.S. PATENT DOCUMENTS

| 7,112,799 B2 | 9/2006 | Vogtmeier |
| 8,357,903 B2 | 1/2013 | Wang et al. |

(Continued)

FOREIGN PATENT DOCUMENTS

| CN | 115244428 A | 10/2022 |
| DE | 102015117494 A1 | 4/2017 |

(Continued)

OTHER PUBLICATIONS

Labella, A. et al., "Toward 100 ps Coincidence Time Resolution Using Multiple Timestamps in Depth-Encoding PET Modules: A Monte Carlo Simulation Study", IEEE Transactions on Radiation and Plasma Medical Sciences, Sep. 2021, pp. 679-686, vol. 5, No. 5.

(Continued)

*Primary Examiner* — David P Porta
*Assistant Examiner* — Casey Bryant
(74) *Attorney, Agent, or Firm* — Scully, Scott, Murphy & Presser, P.C.

(57) ABSTRACT

A multiplexing scheme for both energy and timing information is provided for a particle detection system having an (Continued)

optical sensor array with multiple optical sensors. Each optical sensor is associated with multiple scintillator modules. The system has a segmented prismatoid light guide comprising multiple prismatoid segments. Each segment is associated with multiple optical sensors, where the optical sensors are adjacent. One end each scintillator module is in contact with its associated optical sensor and the other is in contact with its associated segment. Multiple optical sensors may be connected to an energy readout channel, respectively, such that optical sensors associated with the same segments are not connected to the same energy readout channel. Each energy readout channel has at least two timestamps associated therewith.

19 Claims, 31 Drawing Sheets

(51) Int. Cl.
*A61B 6/42* (2024.01)
*G06T 11/00* (2006.01)

(56) References Cited

U.S. PATENT DOCUMENTS

| | | | |
|---|---|---|---|
| 8,669,513 | B2 | 3/2014 | Hughes et al. |
| 9,075,151 | B2 | 7/2015 | Rose et al. |
| 9,304,211 | B2* | 4/2016 | Goertzen ............... G01T 5/08 |
| 9,575,192 | B1 | 2/2017 | Ng et al. |
| 9,696,439 | B2* | 7/2017 | An ..................... G01T 1/2985 |
| 9,995,830 | B2 | 6/2018 | Schulz |
| 10,288,748 | B2 | 5/2019 | Vogtmeier et al. |
| 10,451,748 | B1 | 10/2019 | Qiang et al. |
| 10,527,739 | B2 | 1/2020 | Chappo et al. |
| 11,041,966 | B2 | 6/2021 | Chappo |
| 11,209,556 | B2 | 12/2021 | Wimmers et al. |
| 11,454,730 | B2 | 9/2022 | Goldan et al. |
| 11,782,175 | B2* | 10/2023 | An ..................... H10F 39/1898 250/362 |
| 11,841,470 | B2* | 12/2023 | Goldan ............... A61B 6/037 |
| 2006/0197025 | A1 | 9/2006 | Burr et al. |
| 2013/0334428 | A1 | 12/2013 | Kim et al. |
| 2014/0299777 | A1* | 10/2014 | Oleinik ............... G01T 1/20187 250/366 |
| 2016/0097866 | A1 | 4/2016 | Williams |
| 2016/0223690 | A1* | 8/2016 | Uchida ................ G01T 1/1644 |
| 2017/0045631 | A1* | 2/2017 | An ....................... G01T 1/1644 |
| 2017/0176610 | A1* | 6/2017 | An ..................... H10F 39/1898 |
| 2017/0219724 | A1 | 8/2017 | Marsden |
| 2017/0285182 | A1* | 10/2017 | Fu ..................... G01T 1/2985 |
| 2018/0038966 | A1 | 2/2018 | Fu et al. |
| 2018/0292548 | A1 | 10/2018 | Zhang et al. |
| 2020/0030969 | A1 | 1/2020 | Iwazaki et al. |
| 2020/0233100 | A1 | 7/2020 | Rothschild |
| 2020/0326434 | A1* | 10/2020 | Goldan ............... A61B 6/4225 |
| 2021/0396891 | A1 | 12/2021 | Jacobs et al. |
| 2023/0063565 | A1 | 3/2023 | Ahnen et al. |

FOREIGN PATENT DOCUMENTS

| | | |
|---|---|---|
| JP | 2005539232 A | 12/2005 |
| JP | 2012088306 A | 5/2012 |
| JP | 2017501388 A | 1/2017 |
| JP | 6134455 B1 | 5/2017 |
| JP | 6212501 B2 | 10/2017 |
| JP | 6257928 B2 | 1/2018 |
| JP | 2018529083 A | 10/2018 |
| JP | 6753782 B2 | 9/2020 |
| JP | 2021505896 A | 2/2021 |
| JP | 2022509219 A | 1/2022 |
| JP | 7065843 B2 | 5/2022 |
| KR | 20230041307 A | 3/2023 |
| WO | 2005103759 A1 | 11/2005 |
| WO | 2013186798 A2 | 12/2013 |
| WO | 2020146475 A1 | 7/2020 |
| WO | 2021146559 A1 | 7/2021 |
| WO | 2022/051506 A1 | 3/2022 |
| WO | 2022051579 A1 | 3/2022 |

OTHER PUBLICATIONS

Labella, A. et al., "Prismatoid light guide array for enhanced gamma ray localization in PET: a Monte Carlo simulation study of scintillation photon transport", Physics in Medicine & Biology, Sep. 2020, pp. 1-9, vol. 65, No. 18.
Extended European search report dated Sep. 20, 2024 received in European Patent Application No. 21878505.3.
International Search Report dated Dec. 29, 2021 issued in PCT/US2021/053896.
Written Opinion dated Dec. 29, 2021 issued in PCT/US2021/053896.

* cited by examiner

| 64 SiPM Pixels | 16 ASIC_Energy Channels |
|---|---|
| 1, 3, 5, 7 | 1 |
| 16, 10, 14, 12 | 2 |
| 21, 17, 23, 19 | 3 |
| 26, 32, 30, 28 | 4 |
| 33, 37, 35, 39 | 5 |
| 42, 48, 44, 46 | 6 |
| 49, 51, 53, 55 | 7 |
| 58, 60, 64, 62 | 8 |
| 41, 57, 25, 9 | 9 |
| 50, 34, 18, 2 | 10 |
| 59, 43, 27, 11 | 11 |
| 4, 36, 52, 20 | 12 |
| 61, 29, 45, 13 | 13 |
| 54, 38, 22, 6 | 14 |
| 63, 47, 31, 15 | 15 |
| 24, 8, 56, 40 | 16 |

Fig. 14

| SPTR (ps) | Trigger photon(s) | Depth-Encoding | Classical CTR (ps, Center/Edge/Corner) | CNR CTR (ps, Center/Edge/Corner) |
|---|---|---|---|---|
| 100 | 10 | NO | 204/205/205 | 135(2.3)/136(1.6)/136(1.6) |
| 100 | 10 | YES | 177/217/240 | 117(1.9)/131(2.1)/144(2.5) |
| 100 | 5, 10 | NO | - | 136(1.1)/138(1.8)/139(2.0) |
| 100 | 5, 10 | YES | - | 114(2.0)/120(1.3)/122(1.6) |
| 100 | 5, 10, 50 | NO | - | 124(1.5)/126(1.6)/128(1.1) |
| 100 | 5, 10, 50 | YES | - | 105(1.9)/113(2.1)/119(2.4) |
| 50 | 10 | NO | 162/183/183 | 174(1.5)/176(1.5)/175(0.9) |
| 50 | 10 | YES | 127/183/161 | 81(2.3)/96(1.4)/114(2.0) |
| 50 | 5, 10 | NO | - | 107(1.1)/108(1.4)/108(1.6) |
| 50 | 5, 10 | YES | - | 72(2.0)/78(2.1)/84(1.5) |
| 50 | 5, 10, 50 | NO | - | 92(1.3)/93(1.4)/92(2.0) |
| 50 | 5, 10, 50 | YES | - | 64(1.0)/71(1.0)/67(1.6) |
| 10 | 10 | NO | 177/180/180 | 168(0.7)/170(1.2)/170(1.8) |
| 10 | 10 | YES | 93/119/139 | 71(1.9)/82(1.1)/120(1.5) |
| 10 | 5, 10 | NO | - | 95(1.4)/95(1.5)/97(2.1) |
| 10 | 5, 10 | YES | - | 50(1.3)/59(1.7)/69(2.1) |
| 10 | 5, 10, 50 | NO | - | 83(1.0)/81(1.3)/82(1.4) |
| 10 | 5, 10, 50 | YES | - | 45(1.5)/50(1.5)/56(1.1) |

Fig. 18

SYSTEM AND METHOD FOR POWER-EFFICIENT MULTIPLEXING FOR HIGH RESOLUTION TIME-OF-FLIGHT POSITRON EMISSION TOMOGRAPHY MODULES WITH INTERCRYSTAL LIGHT SHARING

CROSS-REFERENCE TO RELATED APPLICATIONS

This application claims the benefit of and priority to U.S. Provisional Application Ser. No. 63/088,718 filed on Oct. 7, 2020, and U.S. Provisional Application Ser. No. 63/110,109 filed on Nov. 5, 2020, the entirety of each of which is incorporated herein by reference.

FIELD

This disclosure relates generally to the field of radiation imaging and, in particular, to positron emission tomography (PET).

BACKGROUND

Imaging with PET is a powerful technique used primarily for diagnosis, treatment selection, treatment monitoring and research in cancer and neuropsychiatric disorders. Despite its high molecular specificity, quantitative nature and clinical availability, PET has not been able to achieve its full potential as the go-to molecular imaging modality due in large part to its relatively poor spatial resolution. Several attempts have been tried to achieve high resolution PET, including using n-to-1 scintillator modules-to-readout pixel coupling (where n>1) (optical sensor), which enables spatial resolution equal to the size of the scintillator modules without increasing the cost of the readout side (e.g., optical sensor, connectors, readout ASIC). While other attempts including using monolithic scintillator modules with nearest-neighbor positioning algorithms, the n-to-1 coupling light sharing are the most commercially viable option due to their simultaneous depth of interaction (DOI) and time-of-flight (TOF) readout capabilities due to the fact that there is no tradeoff in sensitivity and/or energy resolution.

However, as spatial resolution improves, the amount of data per PET scan greatly increases due to the increased number of voxels. Depth-encoding, which is necessary to mitigate parallax error and fully reap the benefits of high resolution PET, further exacerbates the data size problem since the number of lines-of-response (LORs) increases exponentially as a function of number of DOI bins. Combining high resolution with TOF readout also contributes to larger data size in PET since each channel reads out a timestamp per pixel even though multiple timestamps aren't typically used per event, making this process computationally inefficient.

As the data increases, the number of connections between the optical sensors and readout ASIC increase which in practice will increase the heat generated by the device.

Readout systems generally utilize a one-to-one coupling between readout pixel and channels. However, this readout method is inefficient since not all of the pixels need to be read out per event.

Signal multiplexing, whereby the signals read out by multiple optical sensors (pixels) per event are summed together, has been proposed to reduce the data size and complexity in order to make PET less computationally expensive. However, where the signals are multiplex, solutions must be still able to determine primary optical sensor (pixel) interaction, primary scintillator module interaction, DOI and TOF.

In one or more known systems with multiplexing, the detector modules used don't have depth-encoding capabilities (and thus, the multiplexed readout scheme hasn't been shown to work with DOI readout), which is paramount to achieve spatial resolution uniformity at the system-level or high time resolution capabilities for TOF. The multiplexing schemes may also impact the timing resolution.

SUMMARY

Accordingly, disclosed is a particle detection system which may comprise an optical sensor array, a scintillator array and a segmented light guide. The optical sensor array may comprise a first plurality of optical sensors. Each optical sensor may correspond to a pixel. The scintillator array may comprise a second plurality of scintillator modules. The number of scintillator modules may be greater than the number of optical sensors. Multiple scintillator modules may be in contact with a respective optical sensor at a first end of the respective scintillator modules. The segmented light guide may comprise a plurality of prismatoid segments. The segmented light guide may be in contact with a second end of the second plurality of scintillator modules. Each prismatoid segment may be in contact with scintillator modules that are in contact with at least two different optical sensors. The at least two different optical sensors may be adjacent optical sensors. Each prismatoid segment may be configured to redirect particles between scintillator modules in contact with the respective prismatoid segment.

The system may further comprise a third plurality of energy readout channels. Multiple optical sensors may be connected to an energy readout channel, respectively, such that optical sensors associated with the same prismatoid segment may not be connected to the same energy readout channel. Each energy readout channel may have at least two timestamps associated therewith.

In an aspect of the disclosure, the optical sensors may be arranged in rows and columns. Adjacent optical sensors in a row may be connected to different energy readout channels and adjacent optical sensors in a column may be connected to different energy readout channels.

In an aspect of the disclosure, the system may further comprise at least two comparators connected to the multiple optical sensors for the same energy readout channel, for each energy readout channel. Each comparator (for the same energy readout channel) may have a different threshold. The comparators may be connected to the anode or cathode.

In an aspect of the disclosure, the energy readout channels may be connected to the same or different terminals as the information for timing.

In an aspect of the disclosure, four optical sensors may be connected to the same energy readout channel.

In an aspect of the disclosure, there may be different scintillator module to optical sensor coupling such as four-to-one or nine-to-one.

In an aspect of the disclosure, the system may further comprise a first processor configured to bias the first plurality of optical sensors during readout and receive output via the third plurality of energy readout channels and the at least two timestamps associated with each energy readout channel.

In an aspect of the disclosure, the system may further comprise a second processor in communication with the first processor. The second processor may be configured to determine a timing parameter for an event based on the received at least two timestamps.

In an aspect of the disclosure, the timing parameter may be based on a combination of the at least two timestamps. In some aspects, the timing parameter may be based at least on a fastest timestamp. In some aspects, the timing parameter may be based on a linear regression analysis of the received at least two timestamps.

In an aspect of the disclosure, the second processor may be further configured to determine a time of flight (TOF) between coincident detection modules based on the timing parameter.

In an aspect of the disclosure, the second processor may be further configured to configured to determine at least one of a primary interaction pixel, a primary interaction scintillator module or a depth of interaction for the event. In an aspect of the disclosure, the second processor may select the at least two timestamps associated with the determined primary interaction pixel to determine the timing parameter.

In an aspect of the disclosure, the second processor may be configured to determine the TOF using a machine learning model having input the received at least two timestamps from the coincident detection modules.

BRIEF DESCRIPTION OF THE DRAWINGS

FIG. 14 illustrates a table of the multiplex energy channels in accordance with aspects of the disclosure as also shown in FIG. 1A;

FIG. 18 illustrates a table of simulation results based on one, two or three timestamps, with and with DOI correction showing improved coincidence timing resolution using multiple timestamps in accordance with aspects of the disclosure.

DETAILED DESCRIPTION

Figure 1A:
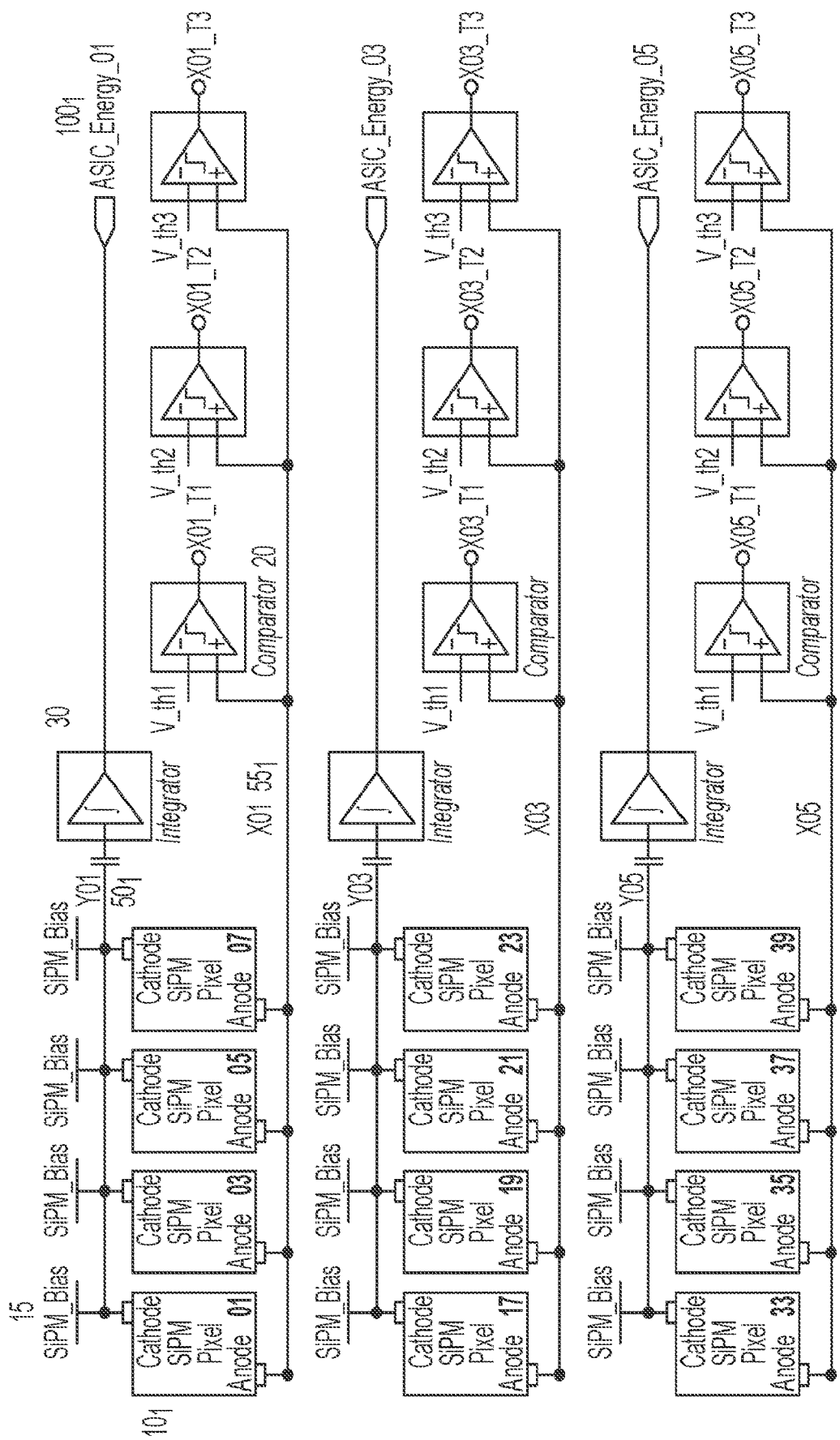
FIG. 1A illustrates a multiplexing scheme in accordance with aspects of the disclosure having cathodes of the optical sensors multiplexed to provide energy information and anodes of the optical sensors multiplexed to provide multiple timestamps in accordance with aspects of the disclosure.
Figure 1A:
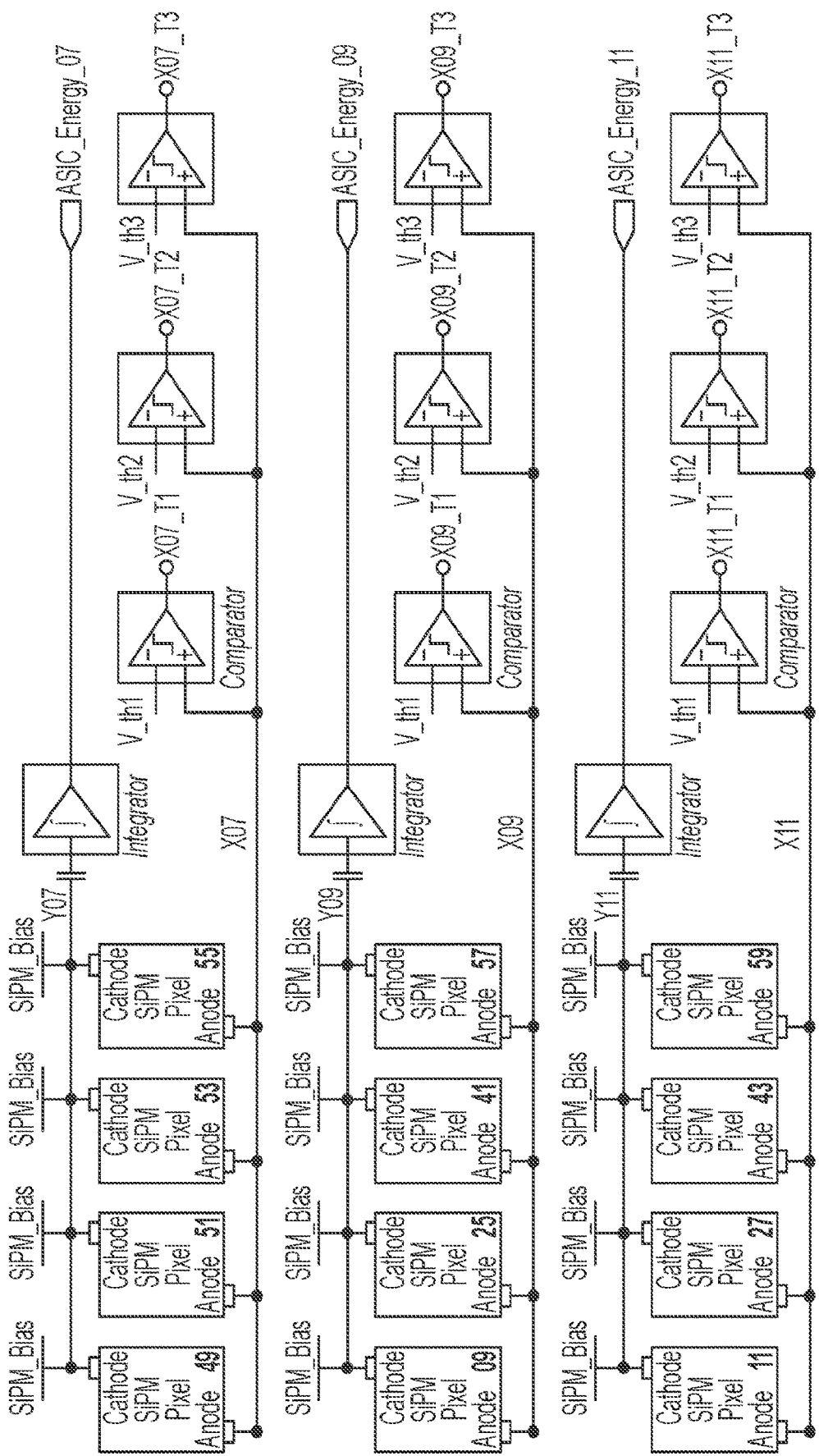
Figure 1A:
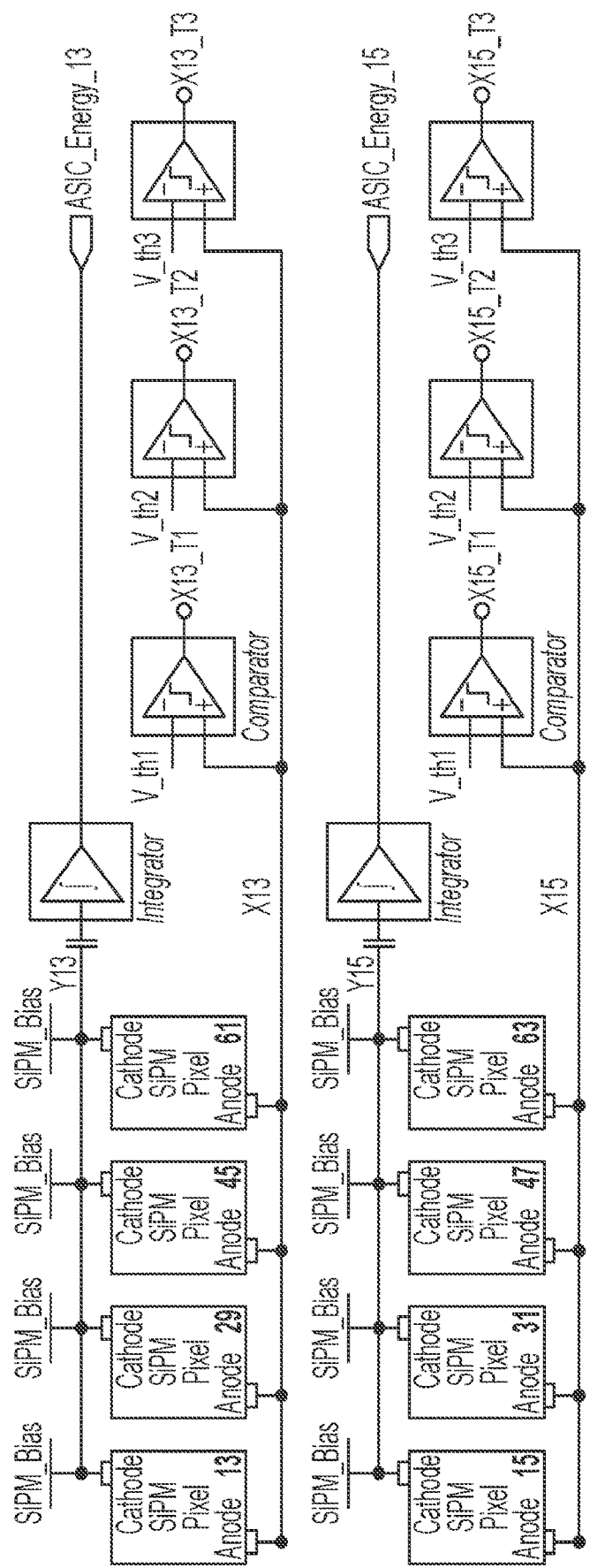
Figure 1A:
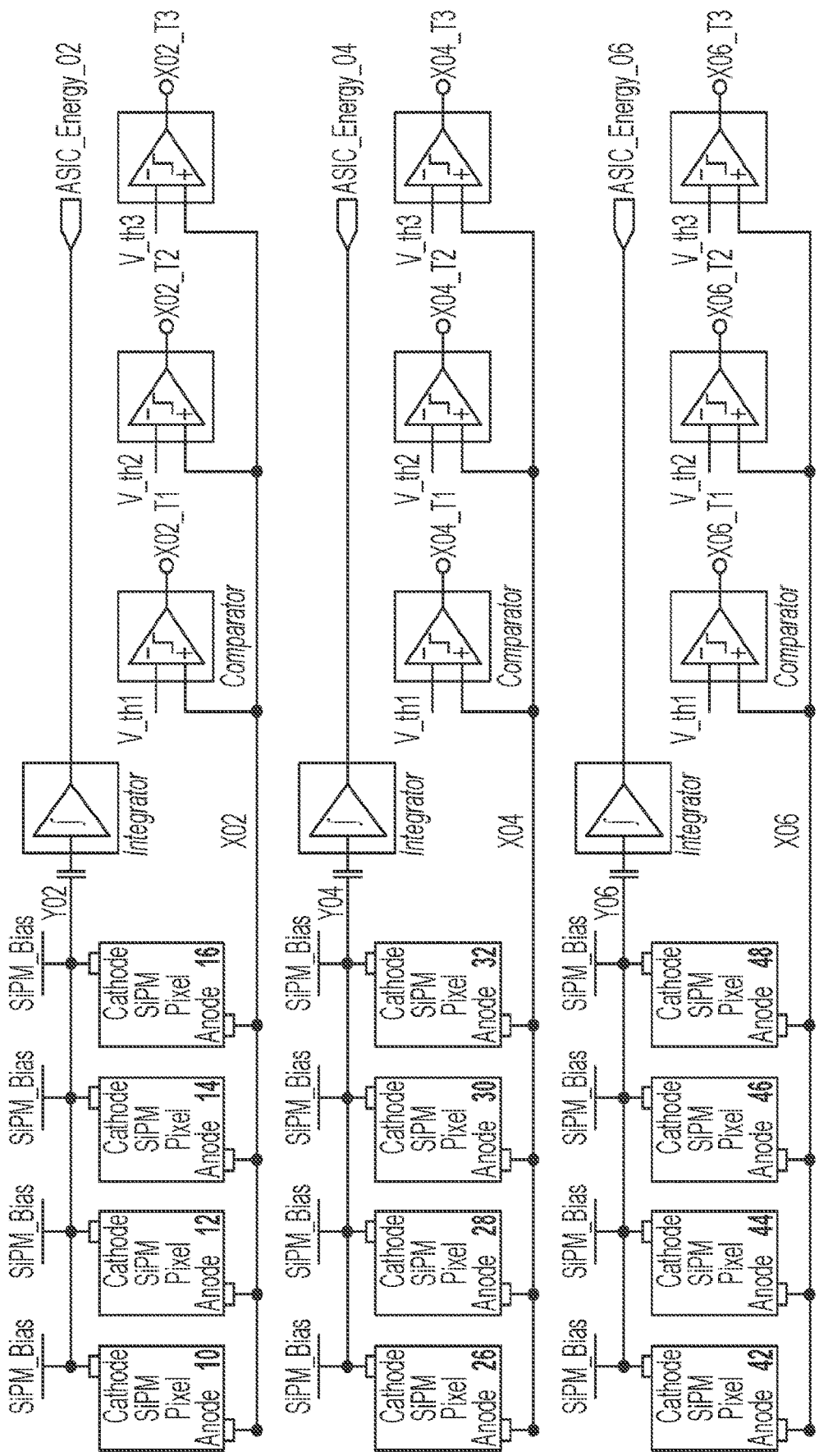
Figure 1A:
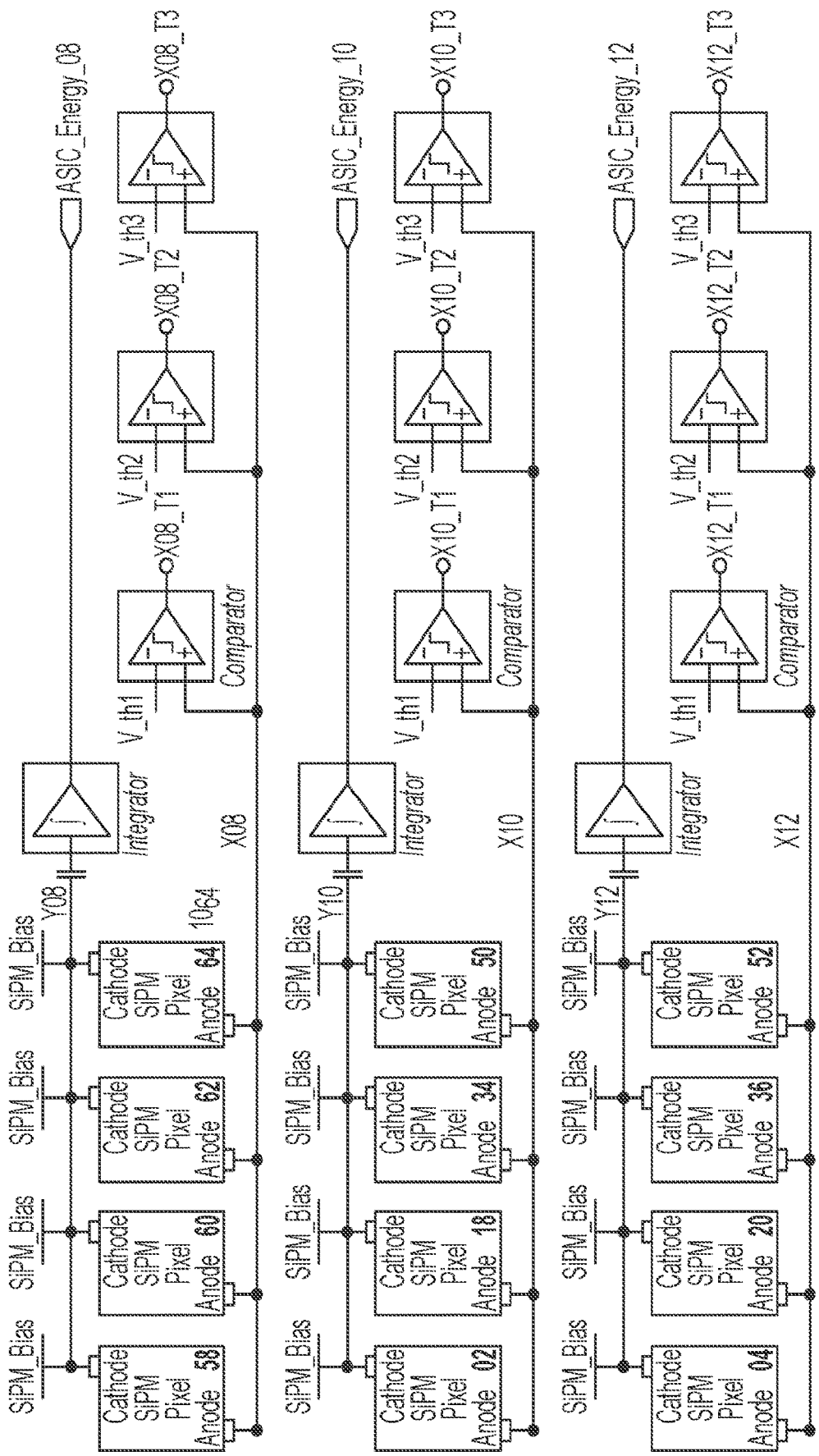
Figure 1A:
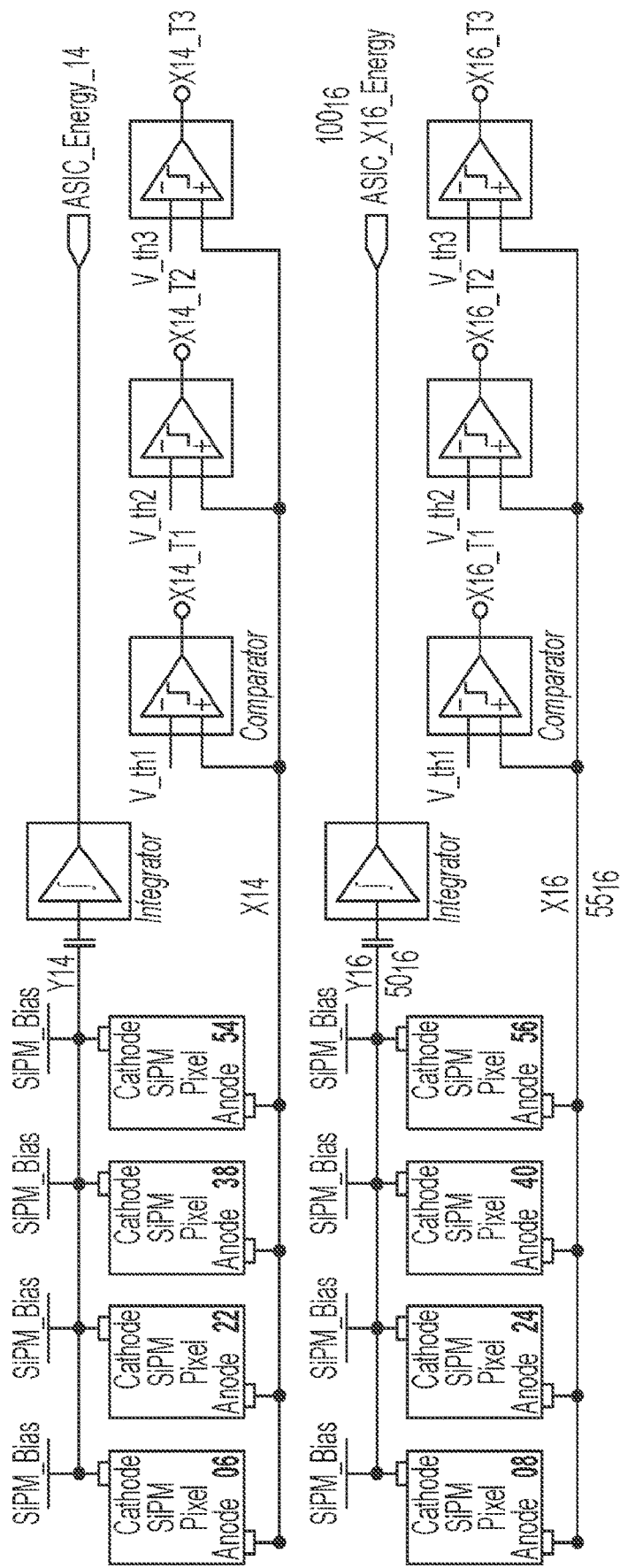

Disclosed is a multiplexing scheme that takes advantage of deterministic light sharing which is enabled using a segmented light guide such as disclosed in U.S. Pat. Pub. No. 2020/0326434 which is incorporated by reference. The particle detection system (and device) described herein has a single-ended readable (with depth-encoding) that has a specialized pattern of segments of a segmented prismatoid light guide. The light guide has prismatoid segments which will be described in detail with respect to at least FIG. 3A. In accordance with aspects of the disclosure, the segmented prismatoid light guide 200 has at least three distinct prismatoid designs, e.g., center prismatoid 162, corner prismatoid 166 and edge prismatoid 168. The prismatoids are designed to mitigate edge and corner artifacts, thereby achieving a uniform crystal identification performance, even when using the multiplexing scheme described herein.

Light sharing between scintillator modules 205 is confined to only scintillator modules 205 belonging to adjacent or neighboring optical sensors 10 (e.g., nearest neighbors) to create a deterministic and anisotropic inter-scintillator module light sharing pattern and maximize signal-to-background ratio on the optical sensors 10 to improve both energy and DOI resolutions while retaining high timing resolution for Time-of-Flight (TOF).

Due to the deterministic light sharing pattern, only a subset of optical sensors 10 (pixels) from nearest neighboring optical sensors (pixels) are required to accurately perform primary optical sensor interaction and DOI (and estimate the primary scintillator module). This is because the relevant signals will be contained within the optically isolated prismatoid segments.

Figure 1B:
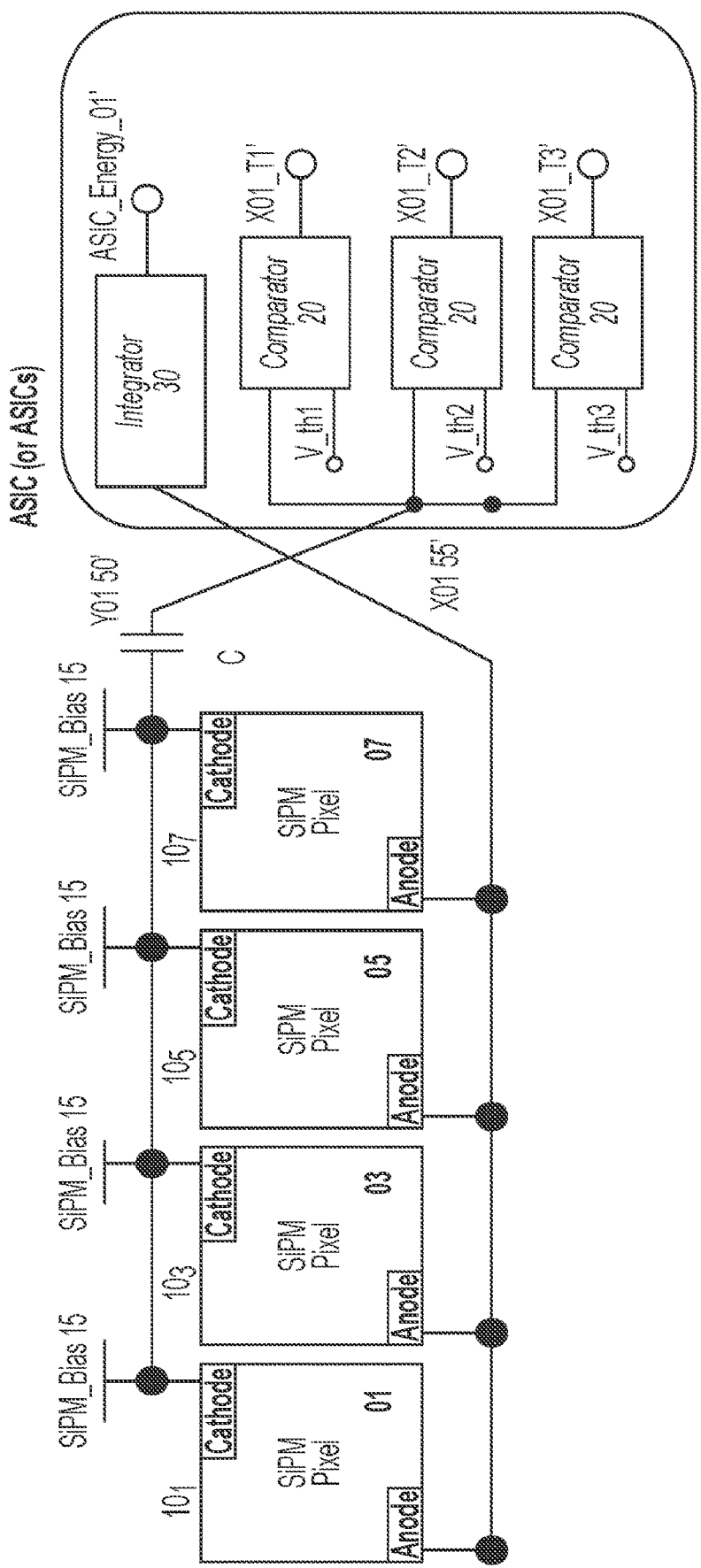
FIG. 1B illustrates a multiplexing scheme for one energy channel and associated timestamps where the anodes of the optical sensors are multiplexed to provide energy information and cathodes of the optical sensors are multiplexed to provide the timestamps.

FIG. 1A illustrates an example of a multiplexing scheme in accordance with aspects of the disclosure. As shown in FIG. 1A, the optical sensors $10_1$-$10_{64}$ (collectively 10) (e.g., optical sensor array 210) are multiplexed. In an aspect of the disclosure, the multiplexing creates multiplexed output Y01-Y16 ($50_1$-$50_{16}$, collectively "50") used to generate a plurality of energy readout channels $100_1$-$100_{16}$. Multiplexed output Y01-Y16 is an input to the readout ASIC 405. As shown in FIG. 1A, there are four optical sensors 10 per energy readout channel. The number of optical sensors, number of optical sensors multiplexed, and energy readout channels are not limited to 64, 4 and 16, respectively. Other combinations may be used. Capacitance C may be connected to the cathodes between the multiplexed output and the readout ASIC 405 when the cathode is also connected to the bias 15 as shown in FIGS. 1A and 1B.

Each optical sensor 10 has an anode and cathode. In FIG. 1A, the cathode is shown on the top of the pixel and the anode is shown on the bottom of each pixel. In an aspect of the disclosure, a bias 15 may be supplied to the cathode via a bias circuit. The bias circuit is not shown in FIG. 1A. The bias circuit may comprise one or more capacitors and one or more resistors.

In an aspect of the disclosure, the optical sensors $10_1$-$10_{64}$ may be arranged in rows and columns. For example, the optical sensor array 210 may be an 8×8 readout array. However, the readout array is not limited to 8×8 and may be other dimensions such as 4×4 or 16×16. In some aspects, the readout array may be an integer multiple of two. The two-dimensional array may be formed in a plane orthogonal to a longitudinal axis of the scintillator module. In an aspect of the disclosure, the optical sensors 10 may be a silicon photomultiplier (SiPM). In other aspects of the disclosure, the optical sensors 10 may be avalanche photodiodes (APDs), single-photon avalanche (SPADs), photomultiplier tubes (PMTs), silicon avalanche photodiodes (SiAPDs). These are non-limiting examples of solid state detectors which may be used. The number of optical sensors 10 (pixels) in the device may be based on the application and size of a PET system. In FIG. 1A, the optical sensors 10 are labeled "SiPM Pixel". The two digit number in the bottom right corner of each pixel represents a pixel number. For example, "01" represents the first pixel and "64" represents the last pixel. The numbers are for descriptive purposes only.

Figure 13:
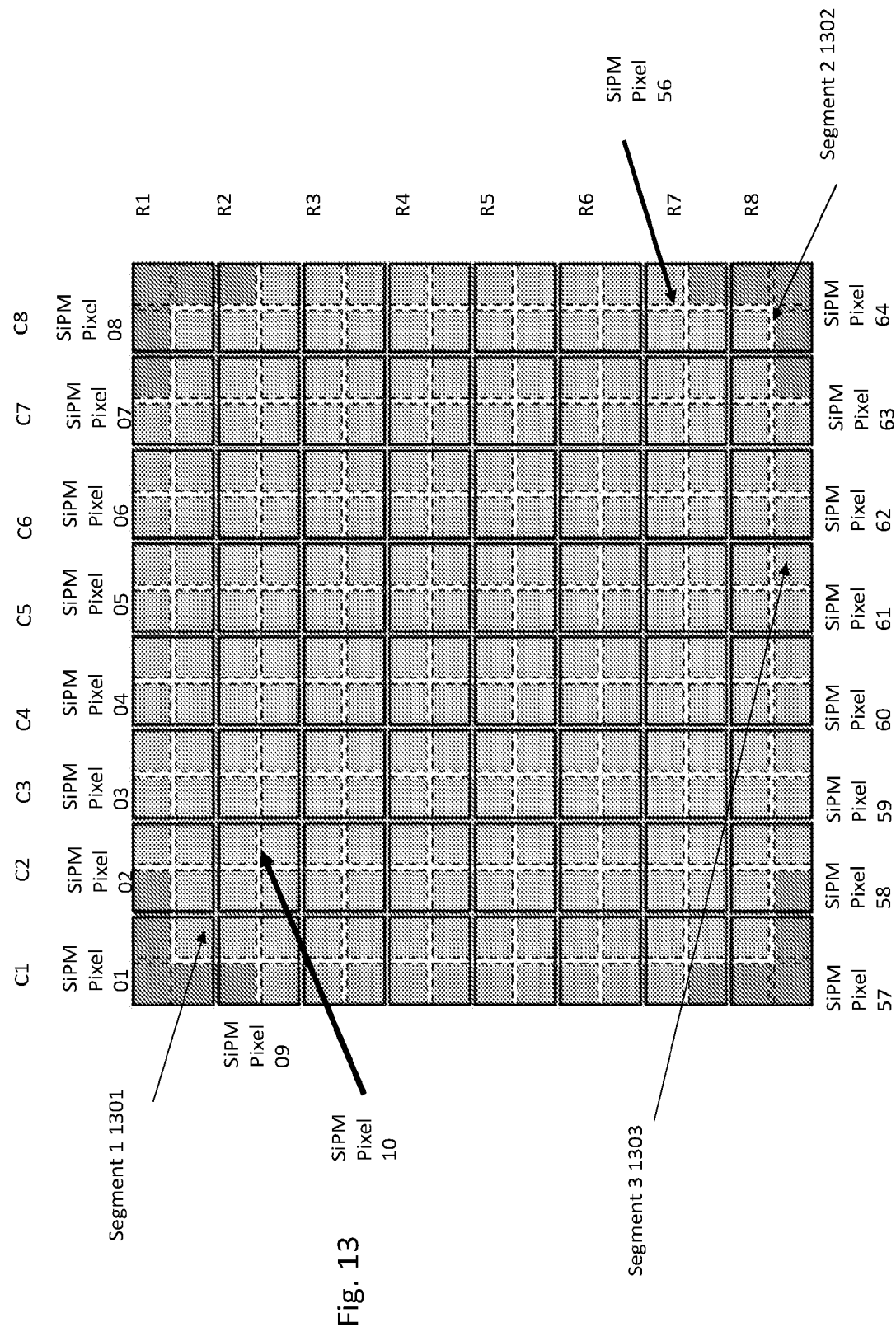
FIG. 13 illustrates an example arrangement of the optical sensor array and segmented light guide in accordance with aspects of the disclosure.

FIG. 13 shows an example of the optical sensor array 210 having an 8×8 configuration (8 rows and 8 columns). In FIG. 13, not all of the optical sensors are number as SiPM Pixel "XX", where XX represents the number.

Optical Sensors (SiPM 01-08) are in a first row, Optical Sensors (SiPM 09-16) are in a second row . . . . Optical Sensors (SiPM 57-64) are in the eighth row (last row). Optical Sensors (SiPM 01, 09, 17, 25, 33, 41, 49 and 57) are in the first column, Optical Sensors (SiPM 02, 10, 18, 26, 34, 42, 50 and 58) are in the second column . . . . Optical Sensors (SiPM 08, 16, 24, 32, 40, 48, 56 and 64) are in the eighth column (last). FIG. 13 also shows an example arrangement of the prismatoid segments of the segmented prismatoid light guide 200 superposed over the optical sensors 10. The optical sensors 10 are shown separated by lines and the scintillator modules (crystals) are represented by dashed lines.

As shown in FIG. 1A, the cathodes of the optical sensors 10 are multiplexed to generate the energy readout channels (via an integrator 30). The signals are integrated by integrator 30 to provide the energy for event(s).

The specific optical sensors 10 multiplexed for a given energy channel are selected such that optical sensors 10 connected to the same segment of the segmented prismatoid light guide 200 are not multiplexed. For example, segment 1 1301 (as shown in FIG. 13) is associated with optical sensors (SiPMs) 01, 02, 09 and 10. As such, light may be shared between the optical sensors (SiPMs) 01, 02, 09 and 10. In accordance with aspects of the disclosure, these optical sensors may not be multiplexed. Similarly, segment 2 1302, is associated with optical sensors (SiPMs) 56, 63 and 64. As such, light may be shared between the same. In accordance with aspects of the disclosure, these optical sensors may not be multiplexed. Similarly, segment 3 1303, is associated with optical sensors (SiPMs) 61 and 62. As such, light may be shared between the same. In accordance with aspects of the disclosure, these optical sensors may not be multiplexed. The arrangement shown in FIG. 13 is similar to the arrangement shown in FIG. 3A.

FIG. 14 shows an example of a multiplexed pattern for the optical sensors 10 where the multiplexed optical sensors in each energy channel are not associated with the same prismatoid segment of the segmented prismatoid light guide (same pattern as in FIG. 1A). In the example, at least one optical sensor 10 (pixel) is between the optical sensors connected to the same energy channel.

For example, in energy channel (ASIC_Energy_01) $100_1$ optical sensors $10_1$, $10_3$, $10_5$, $10_7$ are connected to the channel (for illustrative purposes not all pixels/optical sensors are specifically labelled with a reference 10). Optical sensors $10_2$, $10_4$, $10_6$, $10_8$ are not connected to energy channel (ASIC_Energy_01). In other aspects of the disclosure, Optical sensors $10_2$, $10_4$, $10_6$, $10_8$ may be connected to energy channel (ASIC_Energy_01) $100_1$ and optical sensors $10_1$, $10_3$, $10_5$, $10_7$ may not be connected to energy channel (ASIC_Energy_01) $100_1$.

(ASIC_Energy_01) $100_1$-(ASIC_Energy_08) $100_8$ may also be referred to herein as row channels since optical sensors in a row, respectively, are connected to the same channel (also referred to herein as horizontal).

(ASIC_Energy_09) $100_9$-(ASIC_Energy_16) $100_{16}$ may also be referred to herein a column channels since optical sensors in a column, respectively, are connected to the same channel (also referred to as vertical channels). For example, in energy channel (ASIC_Energy_09) $100_9$, optical sensors $10_9$, $10_{25}$, $10_{41}$, $10_{57}$ are connected to the same energy channel. Optical sensors $10_1$, $10_{17}$, $10_{33}$, $10_{49}$ are not connected to energy channel (ASIC_Energy_09) $100_9$. In other aspects of the disclosure, optical sensors $10_1$, $10_{17}$, $10_{33}$, $10_{49}$ may be connected to energy channel (ASIC_Energy_09) $100_9$ and optical sensors $10_9$, $10_{25}$, $10_{41}$, $10_{57}$ may not be connected to energy channel (ASIC_Energy_09) $100_9$.

As described above, channels are connected such that adjacent pixels in any direction are not connected to the same energy channel.

In an aspect of the disclosure, the subset of optical sensors in a row connected to an energy channel is offset from the subset of optical sensors in adjacent row connected to its energy channel, by column. For example, optical sensors $10_1$, $10_3$, $10_5$, $10_7$ which are connected to (ASIC_Energy_01) $100_1$, are in columns C1, C3, C5 and C7, respectively. Therefore, optical sensors $10_9$, $10_{11}$, $10_{13}$, $10_{15}$, which are also in columns C1, C3, C5 and C7 may not be connected to (ASIC_Energy_02) $100_2$, but rather optical sensors $10_{10}$, $10_{12}$, $10_{14}$, $10_{16}$, which are in columns C2, C4, C6 and C8.

In an aspect of the disclosure, the subset of optical sensors in a column connected to an energy channel is offset from the subset of optical sensors in column row connected to its energy channel, by row. For example, optical sensors $10_9$, $10_{25}$, $10_{41}$, $10_{57}$ which are connected to (ASIC_Energy_09) $100_9$, are in rows R2, R4, R6 and R8 respectively. Therefore, optical sensors $10_{10}$, $10_{26}$, $10_{42}$, $10_{58}$ (in Columns C2) which are also in row R2, R4, R6 and R8 may not be connected to (ASIC_Energy_10) $100_{10}$, but rather optical sensors $10_2$, $10_{18}$, $10_{34}$, $10_{50}$, which are in rows R1, R3, R5 and R7.

In accordance with aspects of the disclosure, the same optical sensors which were multiplexed for energy are also multiplexed to generate at least two timestamps, e.g., timing information. As shown in FIG. 1A, the anodes of the optical sensors are multiplexed for timing, the multiplexed output for timing is shown in FIG. 1A as X01-X16 ($55_1$-$55_{16}$, collectively "55"). X01-X16 may be input to the readout ASIC 405. In an aspect of the disclosure, the anodes may be used because they are generally faster than the cathodes. The anodes are connected to at least two comparators 20 within the readout ASIC 405 (two timestamps). As shown in FIG. 1A, there are three comparators 20 associated with each energy channel. Each comparator 20 is associated with a different voltage threshold. V_th1, V_th2 and V_th3. The voltage thresholds may correspond to different number of photons. The same three voltage thresholds may be used for the comparators associated with the different energy channels ASIC_Energy_01-ASIC_Energy_16 (collectively "100"). When the multiplexed voltage exceeds the respective threshold, the respective comparator 20 will output a change (e.g., X01_T1, X01_T2 and X01_T3 for ASIC_Energy_01 . . . X16_T1, X16_T2 and X16_T3 for ASIC_Energy_16). The time of change for each comparator may be used as the timestamps.

Figure 15:
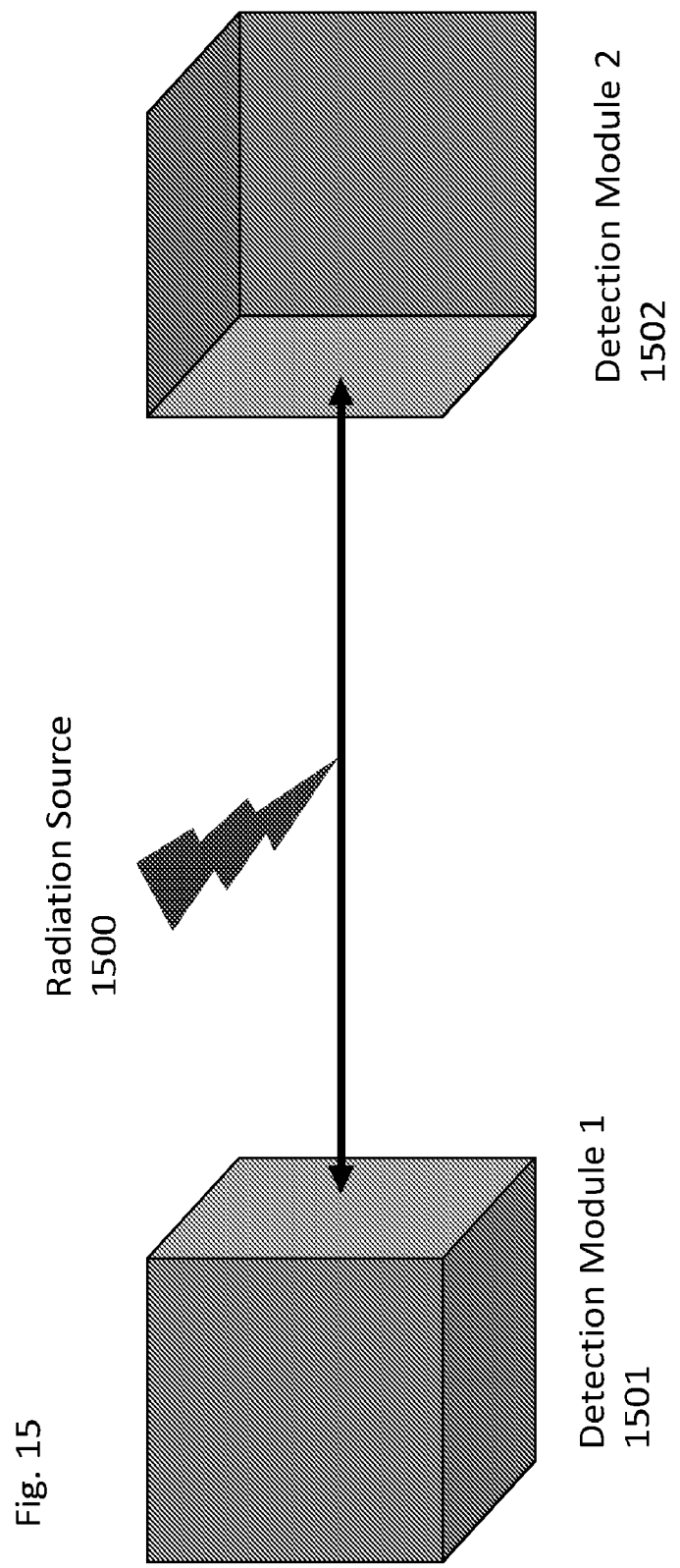
FIG. 15 illustrates an example of coincident detection modules in accordance with aspects of the disclosure.

In some aspects of the disclosure, the timestamps may be combined to determine a timing parameter for an event for the detection device (also referred to herein as detection module). This timing parameter in turn may be used to determine the TOF between coincident detection devices. The TOF may be determined by taking the difference between the timing parameters of two opposing detection devices (coincident). FIG. 15 shows two detection devices (e.g., Detection Module 1 1501 and Detection Module 2 1502) and a radiation source 1500 between them. The radiation source 1500 may be aligned with the center of the two detection devices. Coincidence time resolution (CTR) is a measure of the accuracy in the repeated TOF measurements at the same position of the radiation source 1500 (jitter). CTF is determined by taking the full width at half maximum (FWHM) of the distribution of TOF at a given fixed position.

The CTR may be improved by using multiple timestamps. In some aspects, the use of multiple times may improve the CTR through leading edge slope estimation or waveform shape estimation. The leading edge slope estimation or waveform shape estimation may be done via a machine learning. For example, a convolutional neural network (CNN) may be used as will be described later.

In other aspects, the connections to the readout ASIC 405 may be reversed, and the multiplexed output 55' of the connected anodes may be used for the energy channel(s) as shown in FIG. 1B, e.g., ASIC_Energy_01'. The multiplexed output 50' of the cathodes may be used for the timestamps, e.g., X01_T1', X01_T2' and X01_T3'. FIG. 1B only shows one multiplexed energy channel (and associated timestamps) for discussion purposes; however, the other channels may have a similar configuration.

Figure 1C:
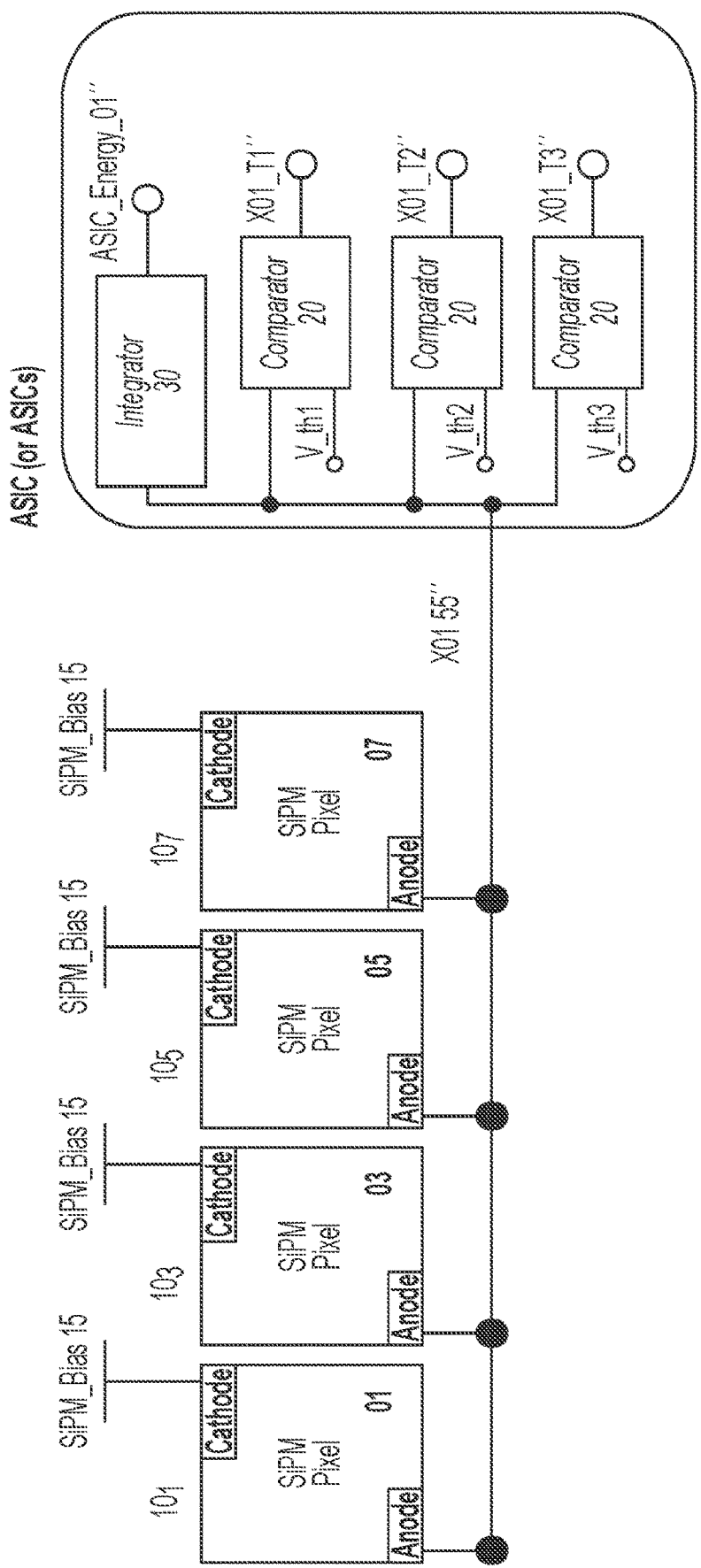
FIG. 1C illustrates a multiplexing scheme for one energy channel and associated timestamps where the anodes of the optical sensors are multiplexed to provide energy information and the timestamps.

In other aspects, the same terminal (e.g., anode or cathode) may be used for both energy and timing information. For example, as shown in FIG. 1C, the anodes of the optical sensors 10 may be multiplexed such that the same multiplexed output 55" is connected to the integrator 30 and comparators 20 to generate the energy channel(s), e.g., ASIC_Energy_01 and the timestamps, e.g., X01_T1", X01_T2" and X01_13". Similar to FIG. 1B, FIG. 1C only shows one multiplexed energy channel (and associated timestamps) for discussion purposes; however, the other energy channels may have a similar configuration.

Multiplexed output Y01-Y16 and Multiplexed output X01-X16 may be connected to a Readout ASIC 405 (also referred herein as first processor). The readout ASIC 405 may comprise the comparators 20 and the integrator 30. When the output changes, the timing is recorded. The Readout ASIC 405 may also comprise analog to digital converters for digitalization of the signals from the optical sensor array 210 and circuitry to control the biasing. The readout ASIC 405 may also comprise a communication interface to transmit the digitized signals to a remote computer 400 (also referred herein as second processor) via a synchronization board 410. The synchronization board 410 synchronizes readouts from different detection devices/Readout ASIC in a PET system. In the system shown in FIG. 2B, only one detection device is shown, however, in practice there are a plurality of detection devices connected to the synchronization board 410. The plurality of detection device may include the opposing detection devices (Detection Modules 1 and 2) 1501 and 1502 shown in FIG. 15. Each detection device may have the 4-to-1 readout multiplexing 1 described herein. The reflector 215 is omitted from FIG. 2B. However, each detection device would have the reflector 215.

Figure 2A:
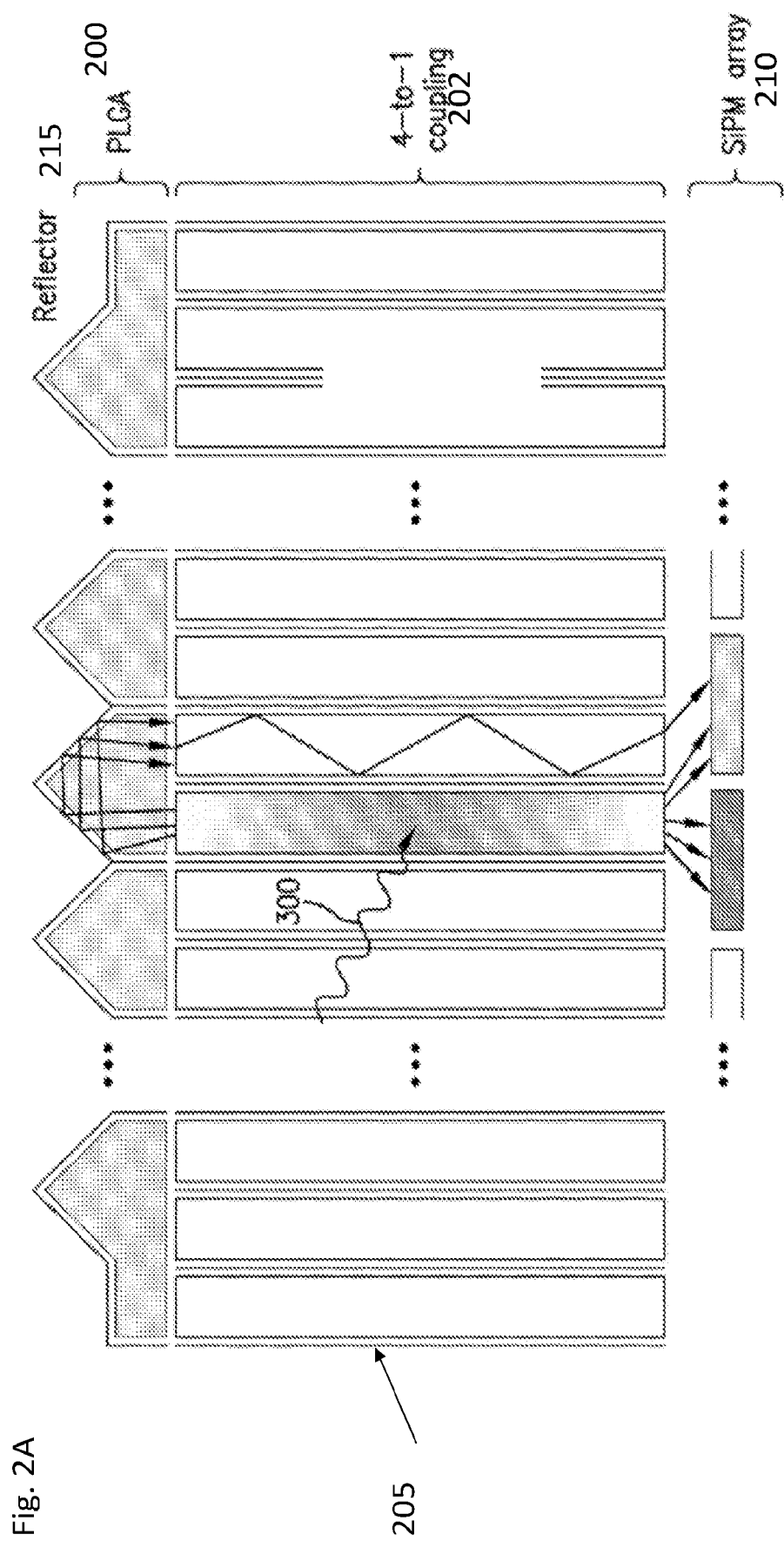
FIG. 2A illustrates a particle detection device having 4-to-1 scintillator module to optical sensor coupling in accordance with aspects of the disclosure.

FIG. 2A illustrates a particle detection device having a 4-to-1 scintillator module to optical sensor coupling 202 in accordance with aspects of the disclosure. Each scintillator module 205 may be fabricated from lutetium-yttrium oxyorthosilicate (LYSO) crystals. The scintillator module 205 is not limited to LYSO and other types of crystals may be used that emits a light photon in the present of incident gamma radiation, such as Lutetium oxyorthosilicate (LSO). In FIG. 2A, the optical sensor array is represented as an SiPM array 210. However, as described above, the array is not limited to an SiPM. The scintillator modules 205 are in contact with a surface of the SiPM array 210 at a first end. While FIG. 2A shows a space between the scintillator modules 205 and the SiPM array 210, in practice, the scintillator modules 205 are attached to the SiPM array 210 via an optical adhesive or epoxy. The optical adhesive or epoxy does not change the path of the particle or light or attenuate the same (if any change, the change is minimal). The space is shown to illustrate the particles travelling from the first end of the scintillator module to the SiPM array (pixel). The scintillator modules 205 are in contact with a surface of the segmented prismatoid light guide (PLGA 200) on a second end. A reflector 215 is positioned above the PLGA 200. In an aspect of the disclosure, the reflector 215 may comprise barium sulfate BaSO$_4$. In other aspects, the reflector 215 may comprise other reflective materials. In an aspect of the disclosure, a reflector 215 may be used between each of the scintillator modules 205. The reflector 215 may also fill any space between the segments of the segmented prismatoid light guide 200.

Figure 3A:
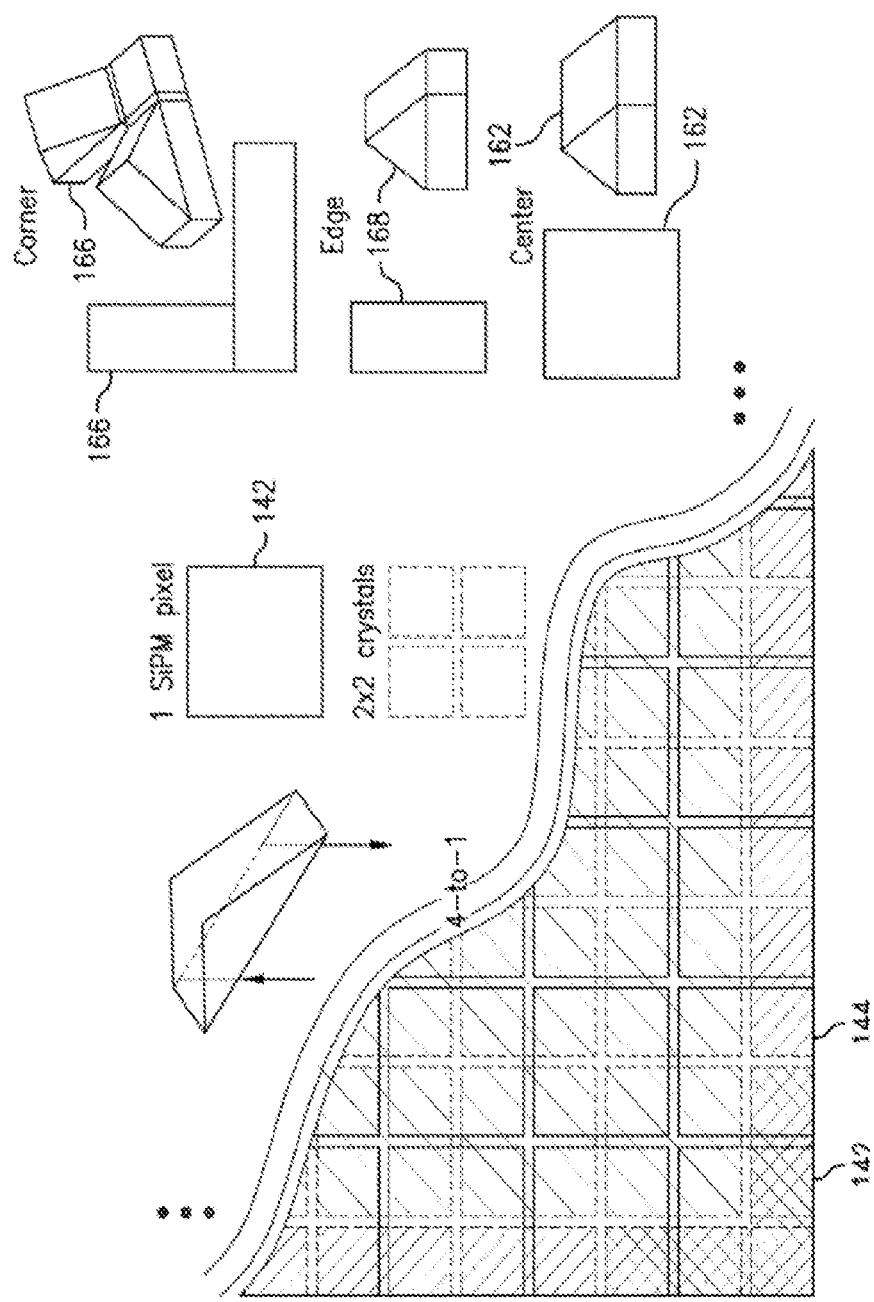
FIG. 3A illustrates a top-down view of a segmented light guide and optical sensors for a 4-to-1 scintillator module to optical sensor coupling, where there are three different designs of segments of the segmented light guide.

FIG. 3A illustrates a view of a segmented prismatoid light guide and optical sensors for a 4-to-1 scintillator module to optical sensor coupling, where there are three different designs of segments of the segmented light guide. The lower left corner of the figure is a plan view illustrating the relative arrange of scintillator modules (2×2) per optical sensor. Also referred to in FIG. 3A as "crystals". Only a subset of the array is shown for illustrative purposes. The three different designs for the prismatoid segments, e.g., center prismatoid 162, corner prismatoid 166 and edge prismatoid 168, are shown with different hashing. The center prismatoid 162 and edge prismatoid 168 are shown with hashing in opposite directions and the corner prismatoid 166 is shown with intersecting hashing. The upper right corner of FIG. 3A illustrates an example of the three different designs (both a sectional view and a perspective view). The corner prismatoid 166 may be in contact with scintillator modules 205 that are in contact with three different optical sensors (three pixels). The edge prismatoid 168 may be in contact with scintillator modules 205 that are in contact with two different optical sensors (two pixels). The center prismatoid 162 may be in contact with scintillator modules 205 that are in contact with four different optical sensors (four pixels).

Figure 3B:
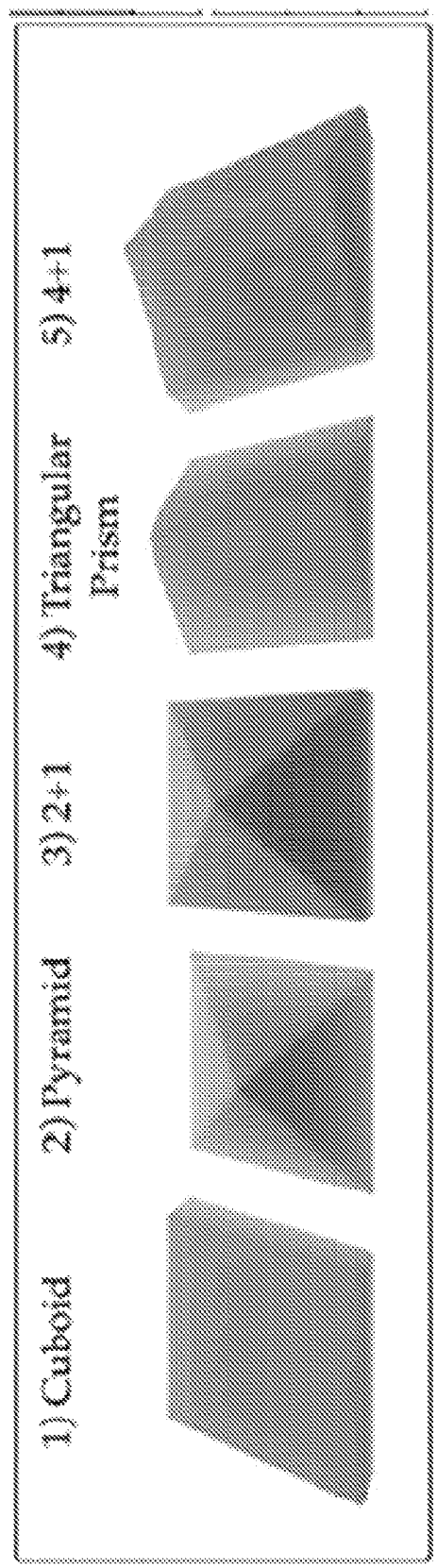
FIG. 3B illustrates examples of 3D views of segments for the segmented light guide in accordance with aspects of the disclosure.

Two adjacent optical sensors are identified using 142 and 144 in FIG. 3A. As shown in FIG. 3A, the prismatoid is substantially triangular in profile shape. However, in other aspect of the disclosure, the prismatoid may be substantially shaped as at least one of at least one prism, at least one antiprism, at least one frustum, at least one cupola, at least one parallelepiped, at least one wedge, at least one pyramid, at least one truncated pyramid, at least one portion of a sphere, at least one cuboid . . . . Examples of certain 3D shapes (five different shapes, for the segments are shown in FIG. 3B. For example, the shapes may be 1) cuboid, 2) pyramid, 3) a combination of a cuboid and pyramid, 4) a triangular prism, 5) a combination of a cuboid and a triangular prism. The combination of a cuboid and a triangular prism is shown in FIG. 3A, where the cuboid forms a base for the triangular prism.

In an aspect of the disclosure, each prismatoid segment of the segmented prismatoid light guide 200 is offset from the optical sensor. In some aspects, the offset is by a scintillator module. In this aspect of the disclosure (and with a 4-to-1 module to sensor coupling), each scintillator module may share light with other scintillator modules from different optical sensors (pixels). For example, when optical photons enter the prismatoid (segment of the light guide) following a gamma ray interaction with a scintillator module 205, the photons (i.e., particles 300) are efficiently redirected to neighboring scintillator modules (of different pixels) due to the geometry, enhancing the light sharing ratio between optical sensors (pixels).

Figure 2B:
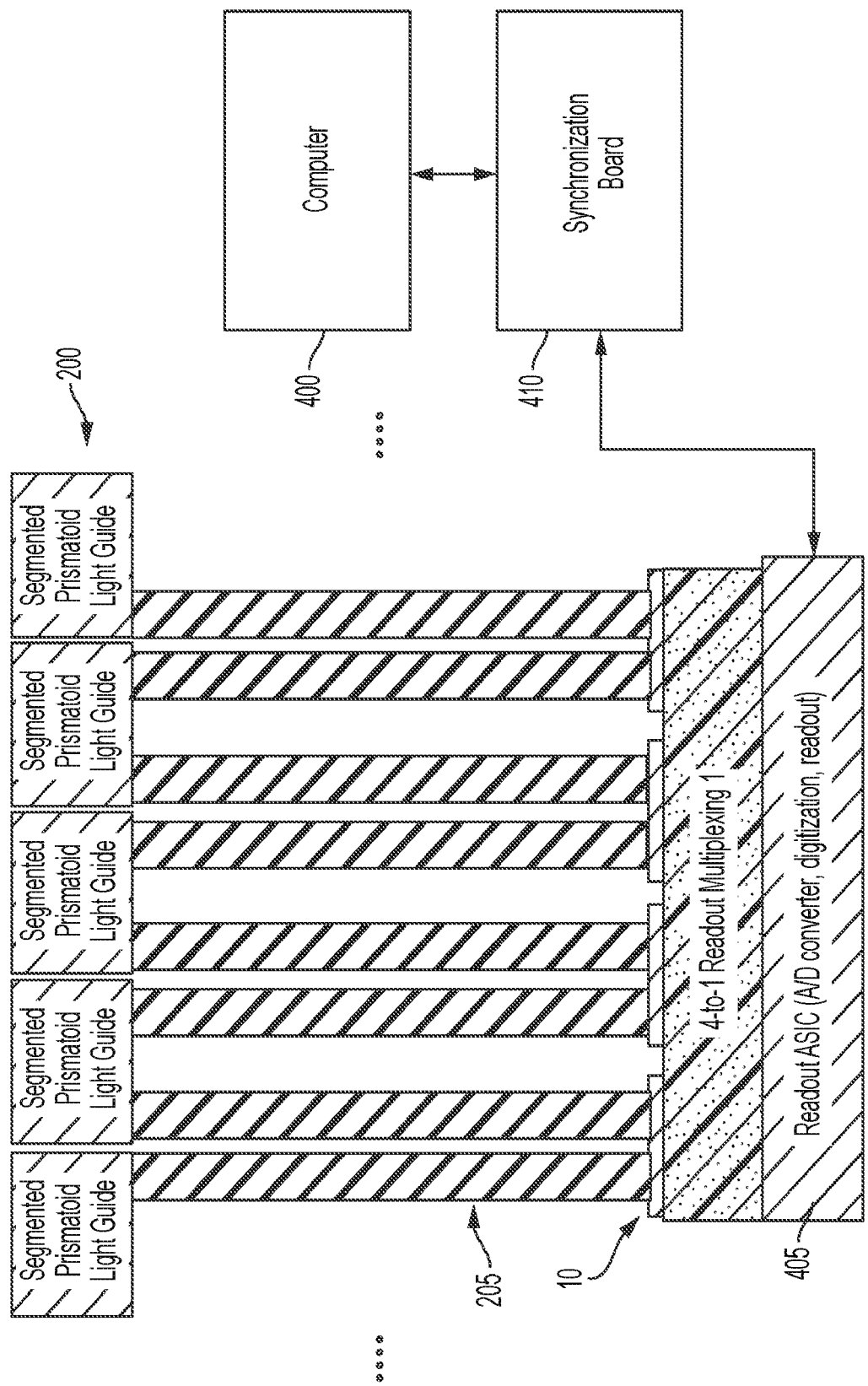
FIG. 2B illustrates a particle detection system in accordance with aspects of the disclosure, where there is a 4-to-1 scintillator module to optical sensor coupling.
Figure 4:
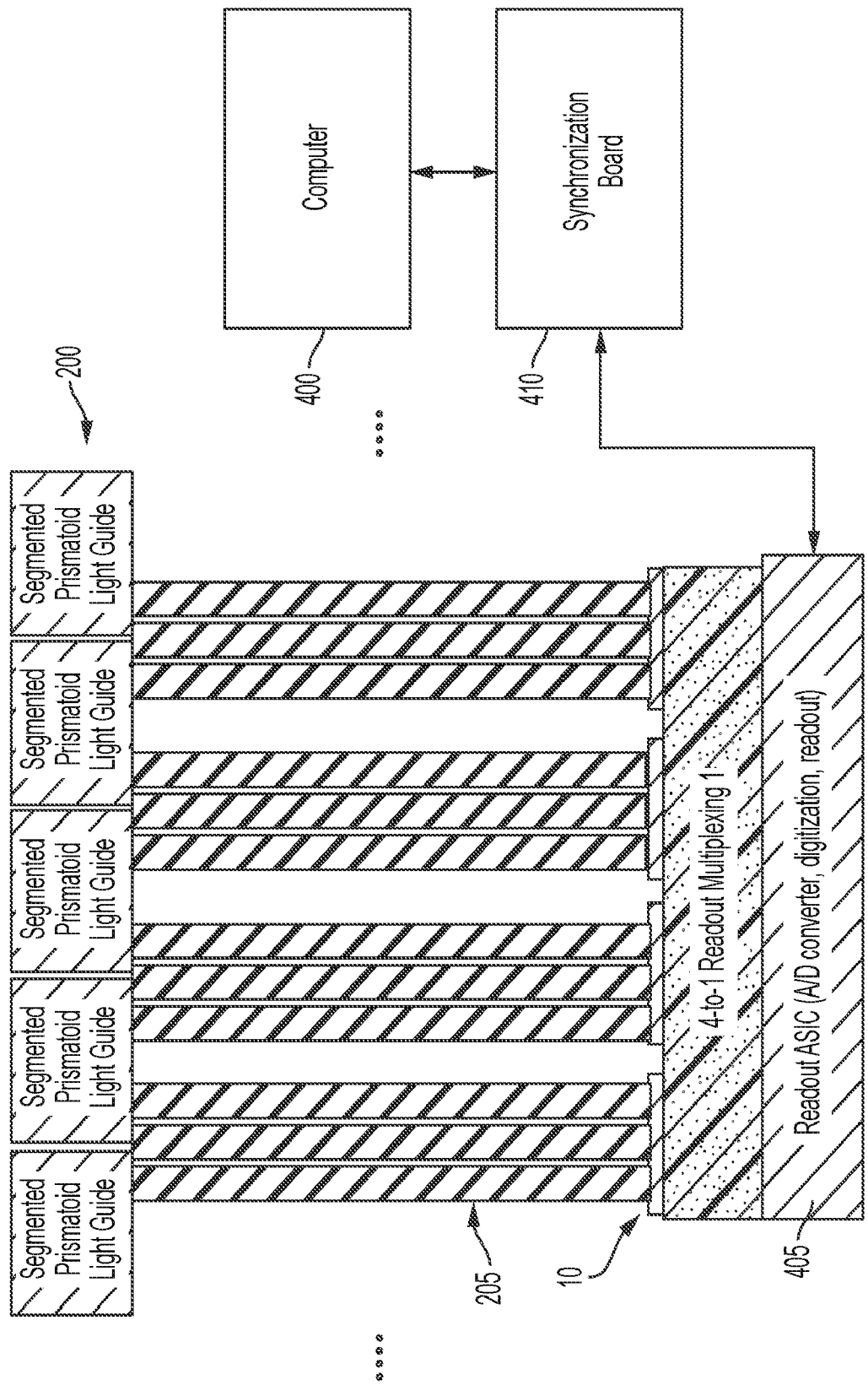
FIG. 4 illustrates a particle detection system in accordance with aspects of the disclosure, where there is 9-to-1 scintillator module to optical sensor coupling.

FIG. 4 illustrates another example of a particle detection system in accordance with aspects of the disclosure. In FIG. 4, there is a 9-to-1 scintillator module to optical sensor coupling. The optical sensors 10 are connected to the readout ASIC 405 in the same manner as described above 4-to-1 readout multiplexing 1 (as shown in FIGS. 1A and 2B). Similar to FIG. 2B, the readout ASIC 405 is connected to the computer 400 via the synchronization board 410. The synchronization board synchronizes readouts from different detection devices/Readout ASIC in the PET system. In the system shown in FIG. 4, only one detection device is shown, however, in practice there are a plurality of detection devices connected to the synchronization board 410. The plurality of detection device may include the opposing detection devices (Detection Modules 1 and 2) 1501 and 1502 as shown in FIG. 15. Each detection device having the 4-to-1 readout multiplexing 1 described herein. The reflector 215 is omitted from FIG. 4. However, each detection device would have the reflector 215. The computer 400 may comprise at least one processor, a memory and a user interface such as a keyboard or/display. The user interface may be used by an operator to specify a readout interval or period.

Figure 5:
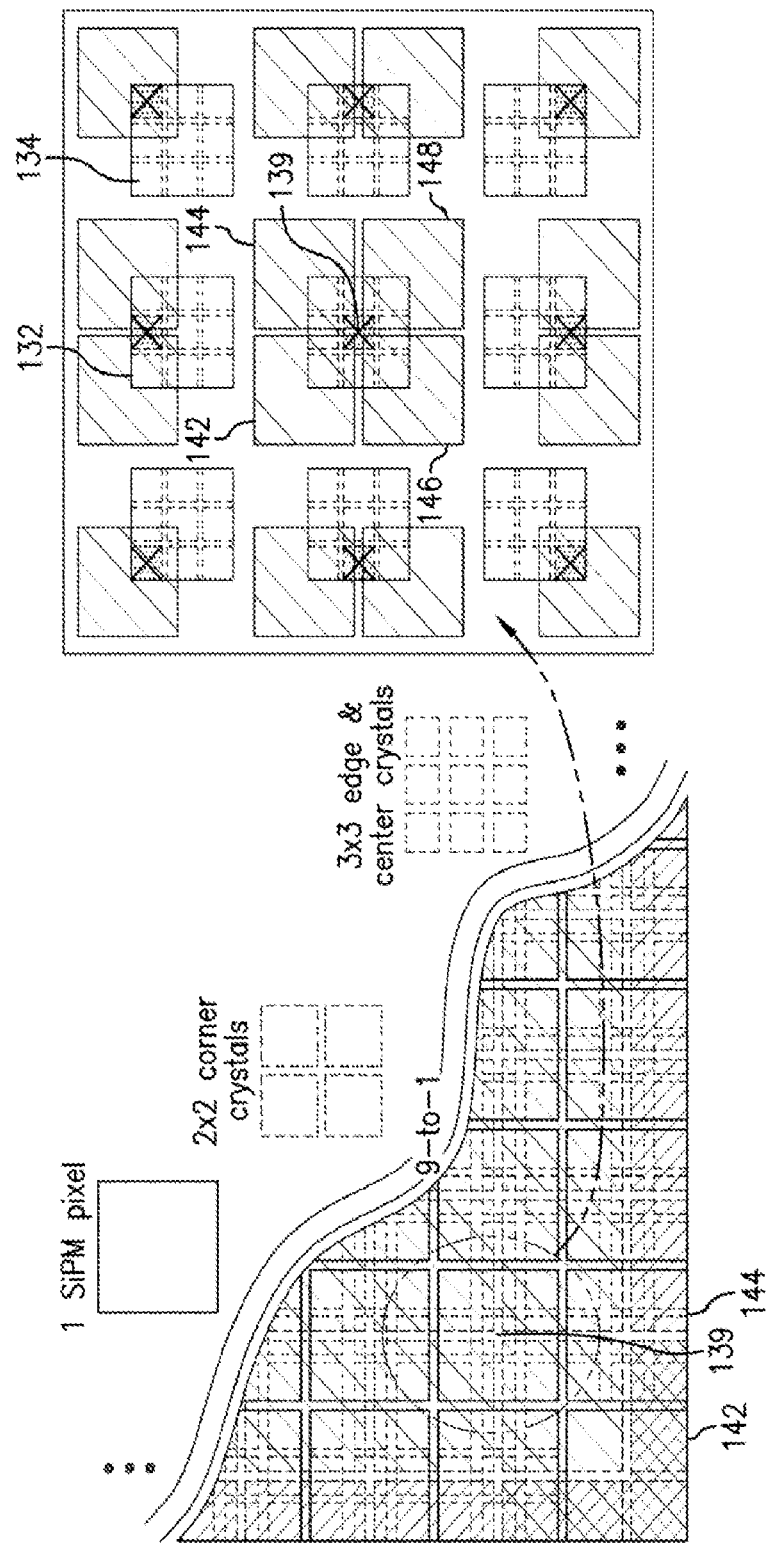
FIG. 5 illustrates a top-down view of a segmented light guide and optical sensors for a 9-to-1 scintillator module to optical sensor coupling, where there are three different designs of segments of the segmented light guide.

In an aspect of the disclosure, each pixel (other than the four corner pixels) may have nine scintillator modules 205. The corner pixels may have four scintillator modules. FIG. 5 shows the segments of the light guide. Similar to FIG. 3A, the different designed segments are shown in the bottom left with different hashing. The bottom left portion of FIG. 5 only shows a representative portion of the array 220. The solid lines around a group of scintillator modules or crystals in the bottom left refers to a pixel (SiPM pixel), whereas the dash lines refers to the modules or crystals. The three different designs for the prismatoid segments, e.g., center prismatoid 162, corner prismatoid 166 and edge prismatoid 168, are shown with different hashing. The center prismatoid 162 and edge prismatoid 168 are shown with hashing in opposite directions and the corner prismatoid 166 is shown with intersecting hashing. The profile of the corner prismatoid 166 for the 9×1 configured may be different from the 4×1 configured since only the corner pixels may have a 4×1 coupling in the 9×1 configuration. The right side of FIG. 5 illustrates several different center prismatoid positions with respect to the pixels (and scintillator modules). Not all SiPM pixels (optical sensors) are shown in the right side of FIG. 5. In FIG. 5, nine center prismatoids are shown to illustrate nine different primary interaction scintillator modules (primary interaction). For example, when the primary interaction scintillator module is module 139 (the center scintillator module in the segment), the segment directs the particles to four adjacent optical sensors/pixels 142, 144, 148, 148. The "X" in FIG. 5 refers to the primary interaction scintillator modules. Segments 132 and 134 may not be adjacent to each other but appear adjacent in the figure.

The corner prismatoid 166 in this configuration may redirect particles between ends of a group of five scintillator modules (three different optical sensors/pixels)(end in contact with the segment). An edge prismatoid in this configuration may redirect particles between ends five scintillator modules as well (two different optical sensors/pixels)(end in contact with the segment).

In other configurations, even the corner optical sensors/pixels 10 may be in contact with nine scintillator modules 205.

In an aspect of the disclosure, the scintillator modules 205 may have a tapered end as described in PCT Application Ser. No. US21/48880 filed Sep. 2, 2021, entitled "Tapered Scintillator Crystal Modules And Methods Of Using The Same" the contents of which are incorporated by reference. The end that is tapered is the first end, e.g., scintillator module/optical sensor interface.

As described above, the deterministic light sharing schemed caused by the segmented light guide 200 guarantees that the inter-scintillator module light sharing only occurs between scintillator modules coupled to the same optically isolated prismatoid light guide and this allows for the multiplexing herein to retain high centroiding, TOF and DOI and energy resolution.

Figure 6:
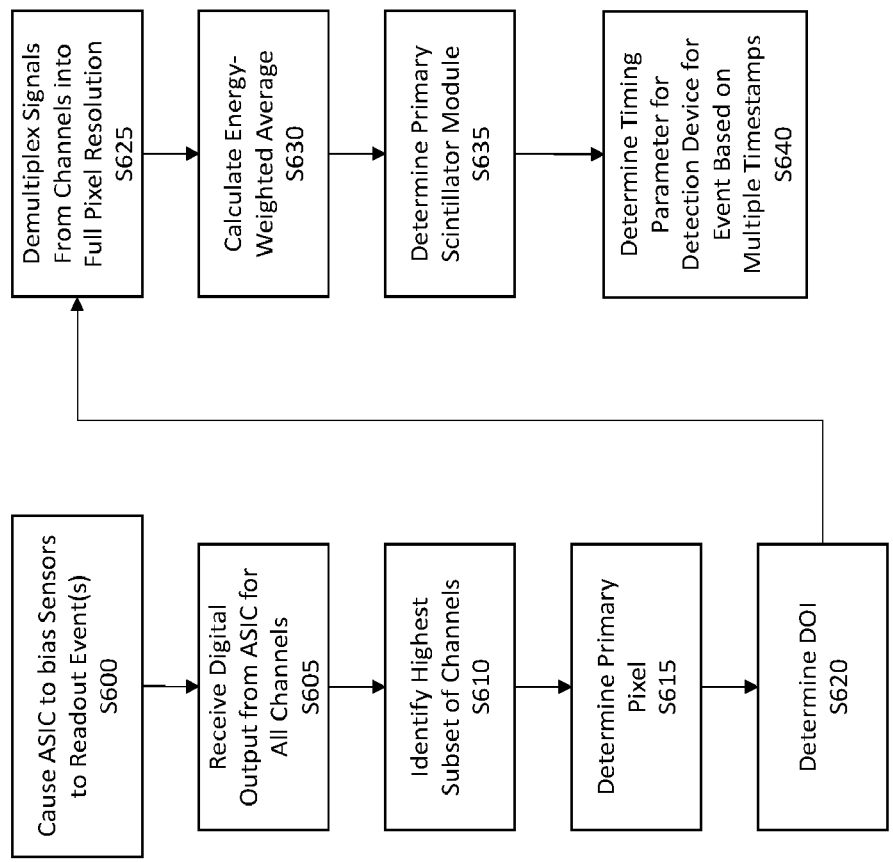
FIG. 6 illustrates a flow chart of a method in accordance with aspects of the disclosure.

FIG. 6 illustrates a flow chart of a method in accordance with aspects of the disclosure. For purposes of the description the functionality describe below is executed by a processor of the computer 400. At S600, the processor issues an instruction to the readout ASIC 405 (via the synchronization board 410) to readout signals from the optical sensor array. This may be in the form of a frame synchronization command. When the readout ASIC 405 receives the instruction, the readout ASIC 405 causes power to be supplied to the optical sensor array 210. In some aspects of the disclosure, there is a switch that is controlled to close to supply a bias. The readout ASIC 405 receives the multiplexed signals Y01-Y16 50 respectively (via connections) for used for energy and X01-X16 55, respectively used for timing (via connections) (or vice versa) or one used for both. The multiplexed signals Y01-Y16 50 may be integrated to get the respective energy channel, digitized and synchronized (via the synchronization board 410) and transmitted to the computer 400. The multiplexed signals X01-X16 may be sent to the comparators 20. Each comparator, respective outputs the values for T1, T2, T3 associated with each energy channel. The timing of the changes may be noted and digitized and transmitted to the computer 400. While FIG. 1A shows three comparators, the number of comparators is not limited to three. In some aspects of the disclosure, at least two comparators may be used.

In other aspects of the disclosure, prior to transmission to the computer, the outputs of the comparators may be combined via one or more logic gates. For example, the outputs from the first comparator may be sent to one logic gate, the outputs from second comparator may be sent to a different logic gate . . . etc.

In an aspect of the disclosure, the computer 400 comprises a communication interface. In some aspects, the communication interface may be a wired interface.

At S605, the processor receives the digitized signals from each of the energy channels ASIC_Energy 01-ASIC_Energy 16 100 and the signals for timing, e.g., digitized outputs from the comparators 20 (associated with each energy channel). In other aspects, the processor may receive the digitized signals from the combined outputs via the logic gates. In some aspects of the disclosure, digitized signals from each of the energy channels ASIC_Energy 01-ASIC_Energy 16 100 are associated with a channel identifier such that the processor may recognize which digitized signals corresponds to which channel. The digitized signals may be stored in the memory. In an aspect of the disclosure, the computer 400 has a preset mapping identifying which pixels are connected to a respective channel (multiplexed). The mapping may be stored in the memory.

At 610, the processor may identify a subset of energy channels ASIC_Energy_01-ASIC_Energy_16 having the highest digitized signals, e.g., highest X energies, for the event (per event). Each event is determined with respect to a time window. The window for an event begins with an initial SiPM sensing a particle(s). The window is "open" for a set period of time. The set period of time may a few nanoseconds. Particles detected within the window (from any SiPM) are grouped and considered as belonging to the same event. In an aspect of the disclosure, the number of relevant energy channels may be based on the location of the event. For example, where the primary interaction is located in the center of the array (associated with a center prismatoid 162), the number of relevant energy channels may be four.

The processor may identify the four energy channels having the four highest digitized signals for the event. When the primary interaction is located at a corner prismatoid 166, the processor may only need to identify three energy channels associated with the three highest digital output. When the primary interaction is located at the edge prismatoid 168, the processor may only need to identify two energy channels associated with the two highest digital output.

Given that the light sharing is optically isolated by the segments, the primary optical sensor (pixel) of interaction, may be determined from the relationship of the energy channels with the certain highest digitized signals. The relationship allows for the unique identification of adjacent optical sensors based on the pattern of the energy channels with the certain highest digitized signals. At S615, the processor may determine the primary interaction optical sensor (pixel). For example, in a case where the primary interaction optical sensor is a center, the processor may determine the relative locations of the identified four energy channels associated with the four highest signals using the stored mapping. This will narrow the primary optical sensor down to the four neighboring optical sensors/pixels (from the 16 possible sensors/pixels connected to the identified channels). For example, when the four highest channels are energy channels ASIC_Energy_02, ASIC_Energy_03, ASIC_Energy_10 and ASIC_Energy_11, the processor may identify SiPM pixels, 10, 11, 18 and 19 as the adjacent optical sensors, e.g., adjacent pixels. Then, the processor may determine which of the four energy channels had the highest signal. The optical sensor (out of the four neighboring optical sensors which were narrowed down) associated with the energy channel having the highest sensor, is identified as the primary optical sensor/pixel (primary interaction). For example, when the maximum signal of the four energy channels is ASIC_Energy_03, the processor may determine that the primary interaction optical sensor (pixel) is 19 (which was narrowed down from 17, 19, 21 and 23 connected to ASIC_Energy_03).

In a case where the primary interaction optical sensor is a corner, the processor may determine the relative locations of the identified three energy channels associated with the three highest signals using the stored mapping. In other aspects, the processor may still use the four energy channels with the four highest signals. This will narrow the primary interaction optical sensor down to three neighboring optical sensors/pixels. Then, the processor may determine which of the three energy channels had the highest signal. The optical sensor (out of the three neighboring optical sensors which were narrowed down) associated with the energy channel having the highest sensor, is identified as the primary optical sensor/pixel (primary interaction).

In a case where the primary interaction optical sensor is an edge optical sensor (associated with the edge prismatoid), the processor may determine the relative locations of the identified two energy channels associated with the two highest signals using the stored mapping. In other aspects, the processor may still use the four energy channels with the four highest signals. This will narrow the primary interaction optical sensor down to two neighboring optical sensors/pixels. Then, the processor may determine which of the two energy channels had the highest signal. The optical sensor (out of the two neighboring optical sensors which were narrowed down) associated with the energy channel having the highest sensor, is identified as the primary interaction optical sensor/pixel.

At S620, the processor may determine the DOI. The DOI may be determined using the following equation:

$$w = \frac{Pmax}{P} \quad (1)$$

Pmax is the digitized value associated with the energy channel having the highest signal (highest energy) for the event and P is the sum of the digitized signals associated with the identified subset of energy channels for the event, which may also be calculated after subtracting out Pmax if desired. Since the segments optically isolate the adjacent optical sensors associated with the segment, the summation is effectively taking the ratio of the energy associated with the primary interaction optical sensor and the sum of the energy of the adjacent sensors. Once the processor identifies the primary interaction optical sensor, then it knows how many energy channels (highest M energy channels) to add, e.g., 4 for the optical sensors for the center prismatoid, 3 for the optical sensors for the corner prismatoid and 2 for the optical sensors for the edge prismatoid.

The ratio may then be converted into a depth using the following equation.

$$DOI = m*w + q \quad (2)$$

where m is the slope between DOI and w according to a best-fit linear regression model, and q is the intercept to ensure DOI estimation starts at DOI=0 mm. Parameters m and q may be determined in advance for the scintillator modules 205.

Therefore, in accordance with aspects of the disclosure, the multiplexed energy signals may be used to determine the DOI and the primary interaction optical sensor without a need to demultiplex the energy signals using the demultiplexing techniques described herein such a machine learning or a look up table. In other aspects of the disclosure, the DOI may be calculated after the multiplexed energy signals are demultiplexed in accordance with aspects of the disclosure and subsequently calculated from the demultiplexed energy signals, where Pmax is the digitized value associated with the optical sensor/pixel having the highest demultiplexed value and p is the sum of all of the demultiplexed values for each optical sensor/pixel.

In an aspect of the disclosure, the primary interaction scintillator module made be estimated using the multiplexed energy signals based on the relative magnitudes of the four highest energy channels. Using the above identified example, when the four highest energy channels ASIC_Energy_02, ASIC_Energy_03, ASIC_Energy_10 and ASIC_Energy_11 is determined, given the light sharing scheme for a center light segment (e.g., prismatoid), the top left scintillating module associated with SiPM 19 may be estimated to be the primary interaction scintillator module. Using the relative magnitudes, the processor may identify the primary optical sensor (pixel), vertical/horizontal neighbors and diagonal neighbors. A diagonal neighbor may have the lowest energy of the identified subset of energy channels. The horizontal/vertical neighbors may have a close energy, e.g., energy channel output may be nearly equal. The adjacent optical sensors identified using the subset of energy channels may be associated with the same segment (due to the light sharing).

While the primary interaction optical sensor and primary interaction scintillator module may be estimated as described above, due to scattering and noise, the same may be determined after the energy signals in the energy channels 100 are demultiplexed as described herein.

At S625, the processor may demultiplex the multiplexed energy signals from the energy channels 100 into a full optical sensor resolution. For example, the processor takes the multiplexed energy signals from the energy channels ASIC_Energy 01-ASIC_Energy 16 100 and generates M×M energy channels of information (number of optical sensors in the system), where M is the number of rows and columns. For example, for a 8×8 readout array, there are 64 demultiplexed energy channels.

In an aspect of the disclosure, the conversion is based on a prestored machine learned model. Generating the machine learned model will be described in detail with respect to FIGS. 7 and 8 later. Specifically, the processor may retrieve the stored machine learned model and using the multiplexed energy signals as inputs to output corresponding 64 energy channels of demultiplexed energy signals corresponding to the 8×8 array.

In other aspects, the processor may use a stored look up table which correlates the multiplexed energy signals into demultiplexed energy signals of full energy channel resolution. The look up table may be created using experimental data obtained from non-multiplexed energy channels. For an 8×8 array, the look up table may be created from 64 energy channels of experimental data taken from a plurality of events. For example, data from the 64 energy channels for an event is obtained. Multiplexed data may be generated by the processor (software-based multiplexing) which adds the same energy channels as shown in FIG. 1A to generate 16 energy channels of data (4 energy channels are added). The 16 energy channels of data are then associated with the 64 energy channels of data for later use. This process may be repeated for a plurality of events to create multiple correspondence information, e.g., 64 energy channels to 16 energy channels. Subsequently, when the multiplexed data is obtained from the readout ASIC 405, the processor looks up the 64 energy channel data. The processor may select the 64 energy channel data that corresponds with the 16 energy channel data that is the closest to the actual detected energy channel data. The closest may be defined as the smallest root mean square error or mean square error. However, other parameters may be used to determine the closest stored 16 energy channel data in the look up table. In other aspects of the disclosure, the processor may interpolate the 64 energy channel data based on the difference between the closest stored 16 energy channel data sets (e.g., two closest).

At S630, the processor, using the demultiplexed energy signals (e.g., signals representing the energy from each optical sensor, to calculate the energy weighted average). The energy weighted average may be calculated by the following equations:

$$u = \frac{1}{P}\sum_{i}^{N} x_i p_i \quad (3)$$

$$v = \frac{1}{P}\sum_{i}^{N} y_i p_i \quad (4)$$

where $x_i$ and $y_i$ are the x- and y-positions of the i-th readout optical sensor (pixel, $p_i$ is the digitized signal readout by the i-th optical sensor (pixel), N is the total number of optical sensors (pixels) in the optical sensor array and P is the sum of the digitized signals from all of the optical sensors (pixels) for a single gamma ray interaction event.

At S635, the processor may determine the primary interaction scintillator module based on the calculated energy weighted average for each scintillator module 205. The scintillator module 205 with the highest calculated energy weighted average may be determined as the primary interaction scintillator module. The optical sensor (pixel) associated with the scintillator module 205 with the highest calculated energy weighted average may be determined as the primary interaction optical sensor (pixel).

In other aspects of the disclosure, instead of determining all three features, e.g., the primary interaction optical sensor (pixel), the primary interaction scintillator module and the DOI, the processor may only determine one of the three features or any combination of the features, e.g., at least one of the three features.

At S640, the processor may determine a timing parameter for the event (for the detection device). This timing parameter may be subsequently used to determine the TOF between detection devices (e.g., Detection Module 1 1501 and Detection Module 2 1502). The timing parameter may be determined based on the timestamp(s) received from the readout ASIC 405. In an aspect of the disclosure, since the primary interaction optical sensor (pixel) may be already determined, the processor may use the timestamp(s) associated with this energy channel to determine the timing parameter. The processor may retrieve from memory the timestamp(s) associated with this energy channel. For example, when SiPM 19 is determined as the primary interaction optical sensor (pixel), the processor may retrieve X03_T1, X03_T2 and X03_T3 from memory. These timestamps were obtained from the comparators 20 (leading edge detectors). In some aspects, the processor may only retrieve X03_T1 since the primary interaction optical sensor typically may have the fastest timestamp. In an aspect of the disclosure, the processor may perform linear regression to determine the timing parameter for the event using the retrieved timestamps, e.g., X03_T1, X03_T2 and X03_T3. In other aspects of the disclosure, the processor may retrieve a machine learned model to predict the TOF (timing offset between the coincident detector devices) (e.g., Detection Module 1 1501 and Detection Module 2 1502).

The machine learning model may be neural network based. However, the machine learning model is not limited to the NN. Other machine learning techniques may be used such as state vector regression. In some aspects of the disclosure, the neural network may be a convolution neural network (CNN), which will be described later.

The use of multiple timestamps may improve the resolution for the CTR because it may eliminate the jitter.

In other aspects, the processor may use the first few determined timestamps to determine the timing parameter. In some aspects of the disclosure, the first timestamp may be determined by combining the timestamps output from comparator with the lowest voltage threshold via a logic gate. Additionally, timestamps may be determined the same way.

In other aspects, the timing parameter may be determined prior to determining the primary interaction optical sensor (pixel).

Figure 7:
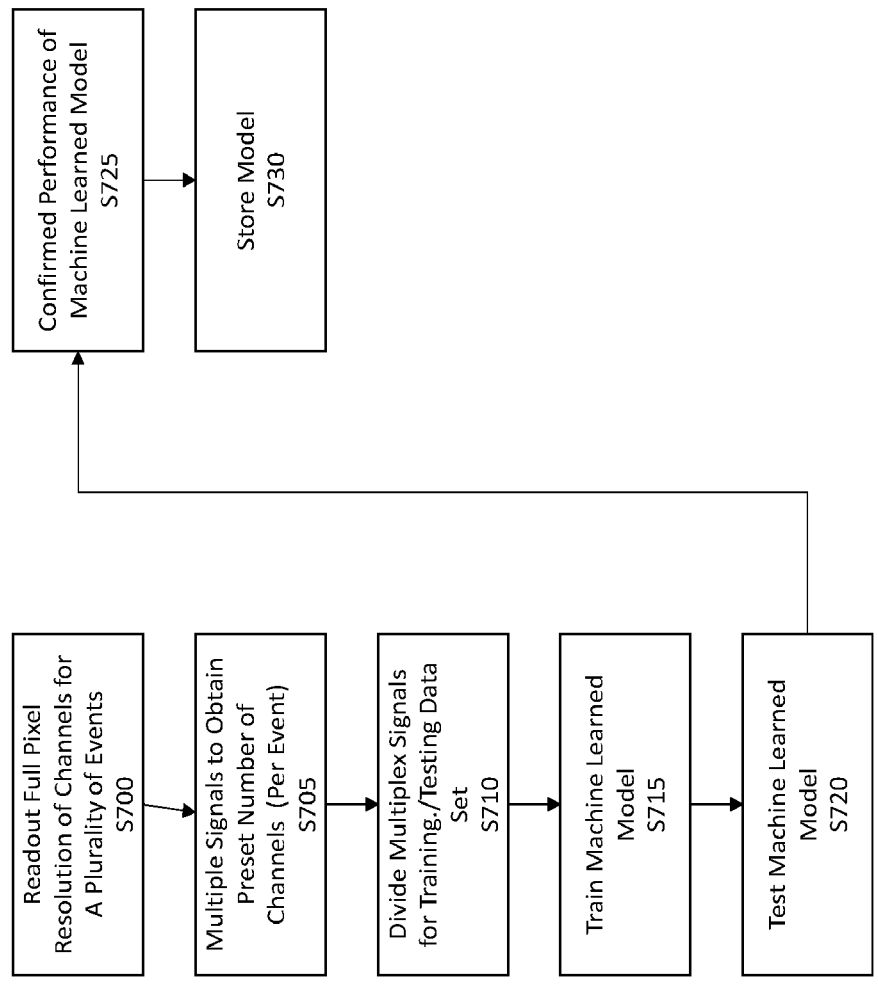
FIG. 7 illustrates flow chart of an example of training and testing of a machine learning model for demultiplexing multiplexed ASIC energy channels in accordance with aspects of the disclosure.

FIG. 7 illustrates flow chart of an example of training and testing of a machine learning model for use in conversion or demultiplexing the energy channels in accordance with aspects of the disclosure. The generation of the machine learning model(s) for use in conversion or demultiplexing the energy channels may be executed on the computer 400. In other aspects, a different device may execute the generating of the models for use in conversion or demultiplexing the energy channels and the same subsequently transmitted to the computer 400.

A different machine learning model (for demultiplexing) may be used for different scintillator module/optical sensor array configurations. For example, a first machine learning model (for demultiplexing) may be used for a 4-to-1 scintillator module to optical sensor array coupling and a second machine learning model (for demultiplexing) may be used for a 9-to-1 scintillator module to optical sensor array coupling (and a third for a 16-to-1 coupling).

A different machine learning model (for demultiplexing) may be used for different scintillator modules (dimensions). For example, with the same coupling (e.g., 4-to-1 scintillator module to optical sensor array coupling), different ML models (for demultiplexing) may be used for scintillator modules having a 1.5 mm×1.5 mm×20 mm verses 1.4 mm×1.4 mm×20 mm. To obtain a dataset for training/testing, the particle detection device including the array of scintillator modules, the segmented light guide and optical sensor array (connected to a readout ASIC) may be exposed to a known particle source. Instead of being multiplexed in accordance with aspects of the disclosure via the connections to the readout ASIC, the optical sensor array is connected to the readout ASIC via N connections, where N is the number of optical sensors 10 in the optical sensor array. The device may be exposed at different depths and over a plurality of events. The digitized signals from each channel (e.g., 64 channels) is recorded per event at S700. This full channel resolution is taken as the ground truth for evaluating the model (during testing).

At S705, multiplex energy signals may be generated by adding a preset number of energy channels for each event. In an aspect of the disclosure, a processor adds the signals from the same optical sensors in accordance with the multiplexing scheme depicted in FIG. 1A to get the multiplex signals. This is to simulate the hardware multiplexing described herein. For example, the processor may add the signals from four optical sensors together to reduce the number of energy channels to 16. The computer-based multiplexed signals may be stored in a memory. At S710, the processor divides the computer-based multiplexed energy signals, generated for each event into a dataset for training and a dataset for testing. In some aspects, 80% of the computer-based multiplexed energy signals may be used for training and 20% may be used for testing and validation. Other divisions may be used such as 75%/25% or 90%/10%. In some aspects, the division may be random.

The machine learning model (for demultiplexing) may be neural network based. However, the machine learning model is not limited to the NN. Other machine learning techniques may be used such as state vector regression. In some aspects of the disclosure, the neural network may be a convolution neural network (CNN). Additionally, in some aspects of the disclosure, the CNN may be a shallow CNN having a U-NET architecture. The hyperparameters including number of convolutional layers, filters and optimizer may be optimized iteratively.

Figure 8:
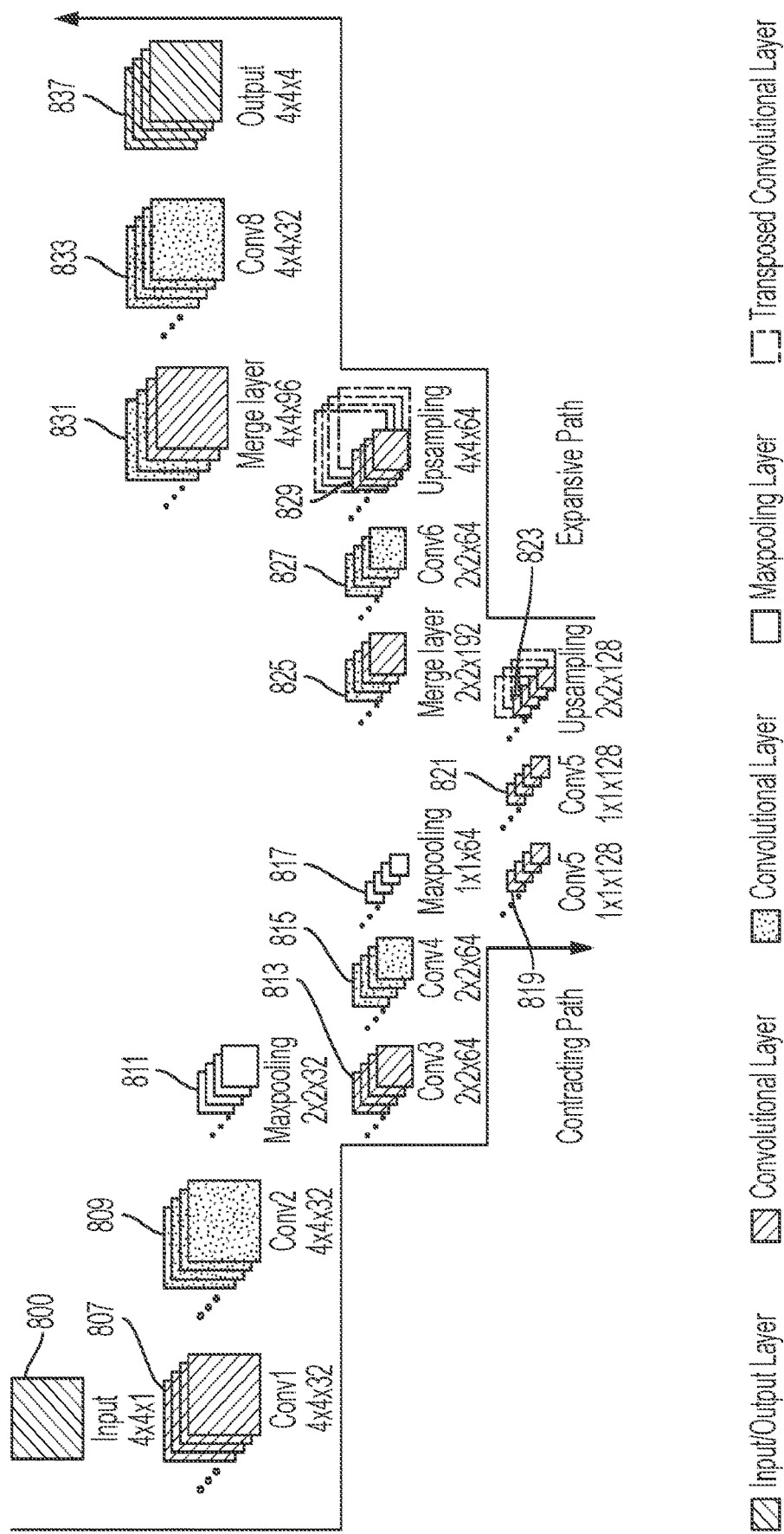
FIG. 8 illustrates an example of a machine learning model demultiplexing multiplexed ASIC energy channels in accordance with aspect of the disclosure.

FIG. 8 illustrates an example of the CNN having the U-NET architecture.

The U-Net consisted of an input layer 800 with the multiplexed data (16×1 which may be reshaped into a 4×4×1 matrix before feeding into the CNN). The input layer 800 may be follows by a series of 2D convolutions such as 807/809 such in FIG. 8. Convolutional layers 807 and 809 may have 32 different 4×4 matrices (also known as "filters").

The convolutional layer 807/809 may be followed by a max-pooling layer 811 to reduce its 2D dimensionality to 2×2, additional convolutional layers 813/815 with 64 filters each, and another max-pooling layer 817 to reduce 2D dimensionality to 1×1. After being reduced to 1×1 dimension space, the matrices may go through several convolutional layers 819/821 with 128 filters each, before undergoing an expansive path to bring it back to its original 4×4 dimensionality and complete the "U" shape.

The expansive path comprises a series of upsampling convolutional layers 823/829 with feature merging with the corresponding layers with equal dimensionality 825/831 and convolutional layers 827/833 with 64/32 filters, respectively. The output layer 837 may be a convolutional layer with 4 filters to provide a 4×4×4 matrix, which may be then reshaped to correlate with the 8×8 readout array. All convolutional layers in the U-Net may have 2×2 filters with stride=1 and may be followed by rectified linear unit (ReLU) activation function. Conceptually, the U-Net may be formulated to demultiplex the single 4×4 matrices (computer-based multiplexed signals) that were fed into the input layer into 8×8 matrices (demultiplexed), which is equal to the number of optical sensors in the array. Note that the shape of the input layer (dimensionality of the matrix) and number of filters in the output layer may be modified based on the readout array being used. For example, the input matrix may be 16×1. Additionally, multiplexed input matrices may be used having smaller dimensions.

The above model may be trained using the training dataset at S715 where the training dataset is input at 800. The above model may be tested using the testing dataset at S720 where the testing dataset is input at 800. The optimizer may be a modified version of Adam optimizer. The initial learning rate may be 1.0. The performance of the model may be evaluated using an evaluation parameter at S725. For example, the evaluation parameter may be mean-squared error MSE. However, the evaluation parameter is not limited to MSE.

Once the model is confirmed using the evaluation parameter, the model may be stored in a memory (in the computer 400) or transmitted to the computer 400 at S730 for subsequent use.

Figure 16:
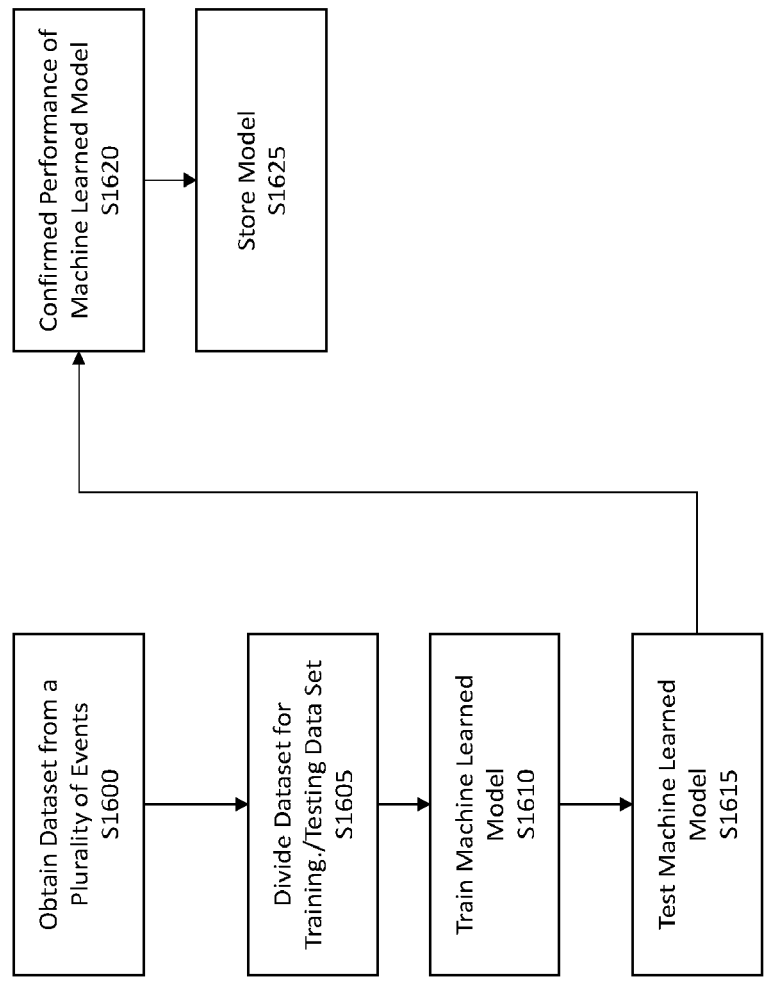
FIG. 16 illustrates a flow chart of an example of training and testing of a machine learning model for use in TOF prediction in accordance with aspects of the disclosure.

FIG. 16 illustrates a flow chart of an example of training and testing of a machine learning model for use in predicting the TOF for coincident detection devices (e.g., Detection Module 1 1501 and Detection Module 2 1502). At S1600, the dataset for training/testing may be obtained. In some aspects of the disclosure, the dataset may be experimentally obtained using a known radiation source 1500 at positions between the Detection Module 1 1501 and Detection Module 2 1502. The position of the radiation source 1500 may be controlled via a fine motor stage. In an aspect of the disclosure, the increments between positions are controlled to be less than the expected CTR. In some aspects, the increments may be smaller than producing a 100 ps CTR. The range of motion of the radiation source 1500 may be 0 to 50 cm. At each positioned, a plurality of events may be detected. For example, the number of events may be 1000. In other aspects, the number of events may be 5000. In other aspects, the number of events may be 10000. In an aspect of the disclosure, the radiation source 1500 may be for a 511 KeV gamma ray absorption. At least two thresholds may be used for leading edge detection.

In other aspects, the dataset for training/testing may be acquired by simulation of events using the parameters of actual detection modules, including length, width, height of the scintillator modules, the photoresponse of silicon photomultipliers with various single photon time resolutions, the coupling, e.g., 4 to 1, reflectors filling between scintillator modules, light sharing segments (shapes), the known response of the scintillator modules to 511 KeV gamma ray interaction, the size of the SiPM, efficiency of the scintillator modules and SiPM.

At S1605, the dataset may be divided into sets for training and testing. In some aspects, 80% of the acquired dataset may be used for training and 20% may be used for testing and validation. Other divisions may be used such as 75%/25% or 90%/10%. In some aspects, the division may be random. In some aspects, a percentage of the dataset may be held out and used for training validation to ensure overfitting does not occur.

Figure 17:
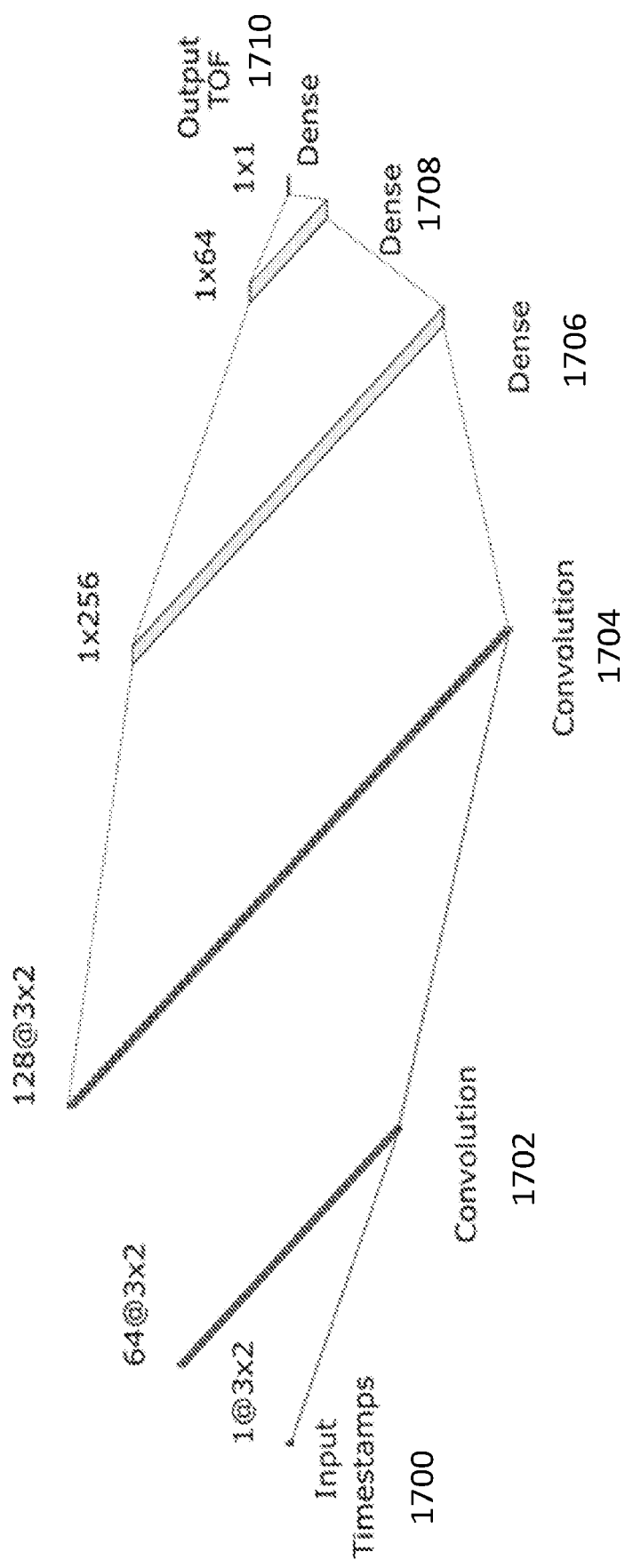
FIG. 17 illustrates an example of a machine learning model for use in TOF prediction in accordance with aspects of the disclosure.

FIG. 17 illustrates an example of a CNN which may be used for predicting the TOF (output TOF) in accordance with aspects of the disclosure. The input may have one input layer. The input layer may include the at least two timestamps per event from each of the coincident detection devices, e.g., Detection Module 1 1501 and Detection Module 2 1502. As shown in FIG. 17, three timestamps (three thresholds) for each detection device are used. Thus, the input layer is 1 @ 3×2 (three timestamps for the two detection devices). The input layer is feed into a convolutional layer 1702. There are 64 filters in convolutional layer 1702. The second convolutional layer 1704 has 128 filters. The filters may be 1×1 filters, stride of 1 and have rectified linear unit (ReLU) activation functions. The CNN may also comprise two fully connected (Dense) layers 1706 and 1708 with ReLU activation. Dense layer 1706 has 256 filters (weights) and Dense layer 1708 has 64 filters (weights). The output Toff (e.g., TOF) is output via a fully connected layer (Dense layer 1710). This layer 1710 has one filter with linear activation.

The above model may be trained using the training dataset at S1610 where the training dataset is input at 1700. The above model may be tested using the testing dataset at S1615 where the testing dataset is input at 1700. Stochastic gradient descent (SGD) with momentum may be used for training optimization with an initial learning rate of 0.01. The performance of the model may be evaluated using an evaluation parameter at S1620. For example, the evaluation parameter may be mean-squared error MSE. However, the evaluation parameter is not limited to MSE.

Once the model for predicting TOF is confirmed using the evaluation parameter, the model may be stored in a memory (in the computer 400) or transmitted to the computer 400 at S1625 for subsequent use.

Testing and Simulation

The multiplexing scheme described above and demultiplexing using machine learning model(s) for demultiplexing the multiplexed energy channels was tested for both a 4-to-1 scintillator module and optical sensor array coupling and a 9-to-1 scintillator module and optical sensor array coupling.

The scintillator modules were fabricated using LYSO and were coupled to an 8×8 SiPM array (optical sensor array) on one end and the segmented prismatoid light guide as described above on the other end. The scintillator module array for the 4-to-1 scintillator module and optical sensor array coupling consisted of a 16×16 array of 1.4 mm×1.4 mm×20 mm, while the scintillator module array for the 9-to-1 scintillator module and optical sensor array coupling consisted of a 24×24 array of 0.9 mm×0.9 mm×20 mm.

Standard flood data acquisition was acquired from both scintillator module arrays (and sensors) by uniformly exposing them with a 3 MBq Na-22 sodium point source (1 mm active diameter) place 5 cm away (at different depths). Depth-collimated data at 5 different depths along the 20 mm scintillator module length (2, 6, 10, 14 and 18 mm) was acquired using lead collimation (1 mm pinhole) to evaluate DOI performance. Data readout was expedited with an ASIC (TOFPET2) and a FEB/D_v2 readout board (PETsys Electronics SA). Computer-based multiplexing was done as described above to achieve a 16×1 scintillator module to energy channel multiplexing for the 4-to-1 scintillator module to optical sensor coupling and a 36×1 scintillator module to energy channel multiplexing for the 9-to-1 scintillator module to optical sensor coupling.

Photopeak filtering using the computer-based multiplexing was performed on a per scintillator module basis with a +−15% energy window. Only events where the highest signal was greater than twice the second signals were accepted in order to reject Compton scatter events with the photopeak.

Demultiplexing the energy signals generated via the computer-based multiplexing was done using the method described above via the machine learning (CNN with U-Net architecture). U-Net training was carried out using 80% of the total dataset. 10% of the training dataset was held out and used for training validation to ensure overfitting wasn't occurring. Adadelta, a modified version of the Adam optimizer was used for training optimization.

A batch size of 500 and 1000 epochs were used for training. Training loss was calculated by taking the average difference between the model estimation and ground truth values across all events for each epoch. Model training was done to reduce loss between successive epochs until a global minimum was found. Model convergence was observed by plotting the training and validation loss curves as a function of epochs and ensuring that they reached asymptotic behavior with approximately equal minimums.

Figure 9A:
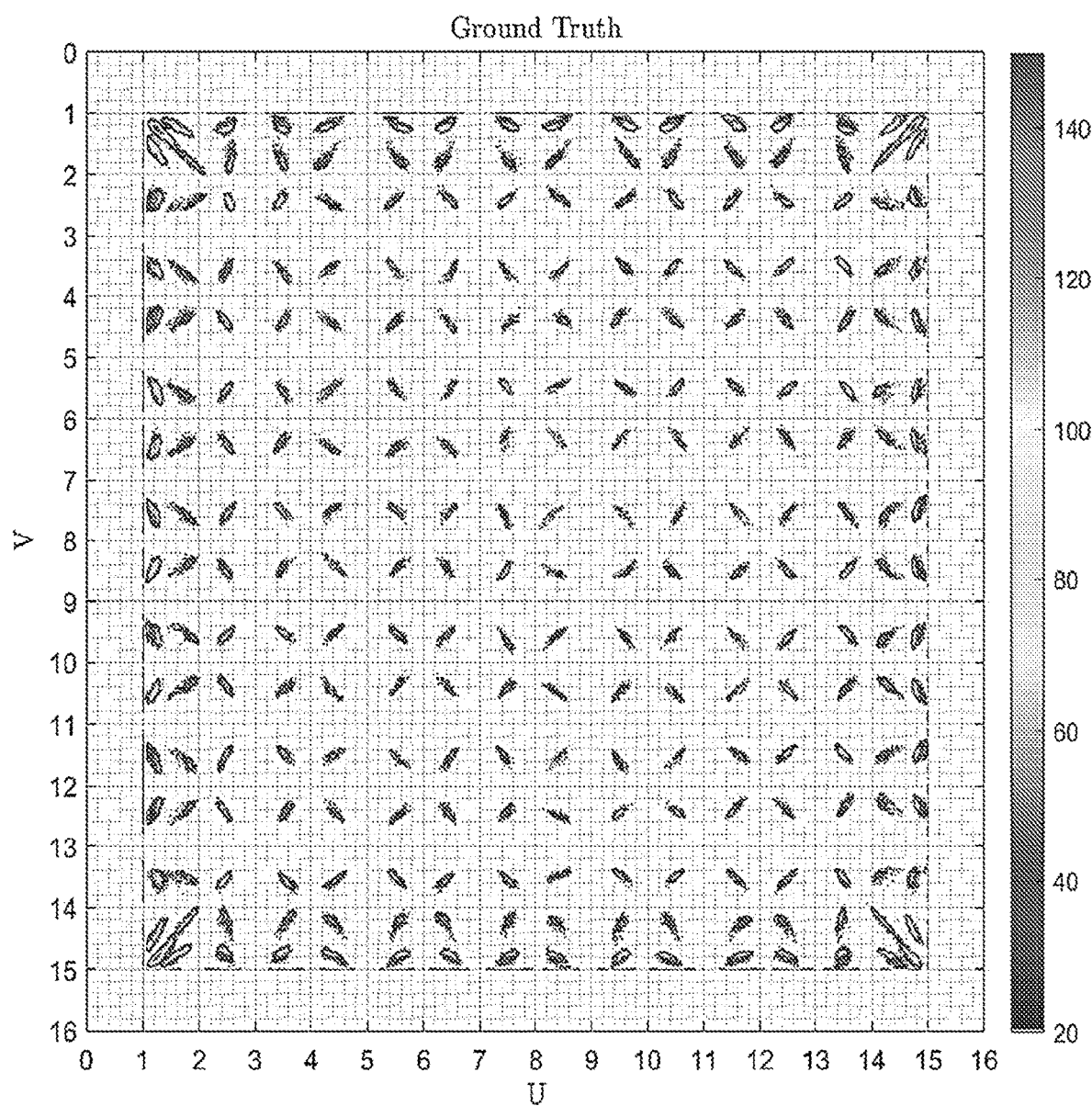
FIG. 9A and FIG. 9B illustrate a comparison between a ground truth and demultiplexing the multiplexed signals using the machine learning model in accordance with aspects of the disclosure for a 4-to-1 scintillator module to optical sensor coupling.
Figure 9B:
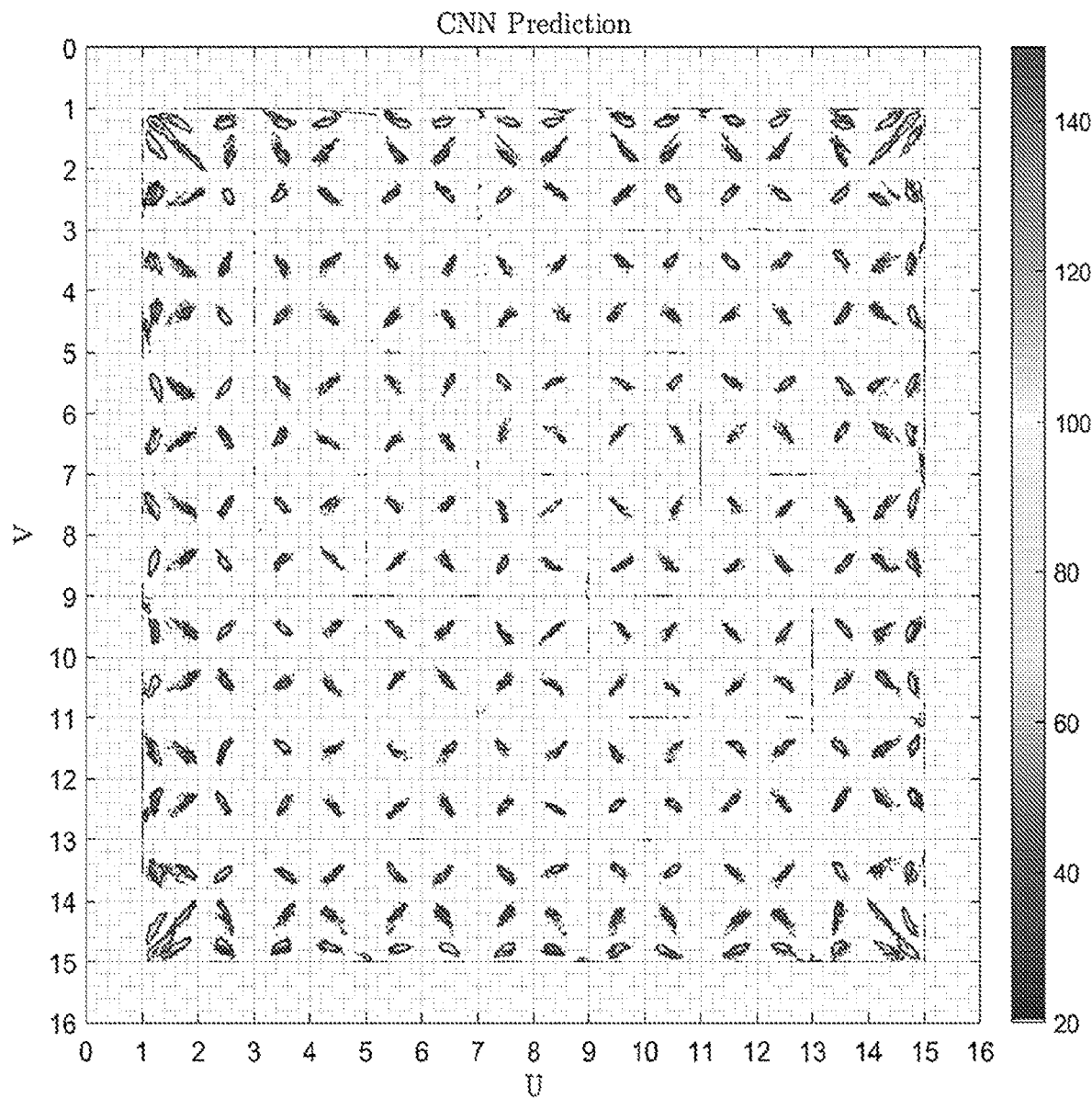

FIGS. 9A and 9B illustrate a qualitative comparison of the actual energy signals output from each of the plurality of optical sensors (without multiplexing) and predictions obtained from the trained/tested machine learning model on computer-based multiplexed energy signals using the multiplexing scheme described herein (demultiplexed) from the 4-to-1 scintillator module to optical sensor coupling. The results appear to be similar. For example, as comparison shown that perfect scintillator module separation was achieved in all center, edge and corner scintillator modules both with and without computer-based multiplexing (of the per-pixel channels). U is on the x-axis and V is on the y-axis.

Figure 9C:
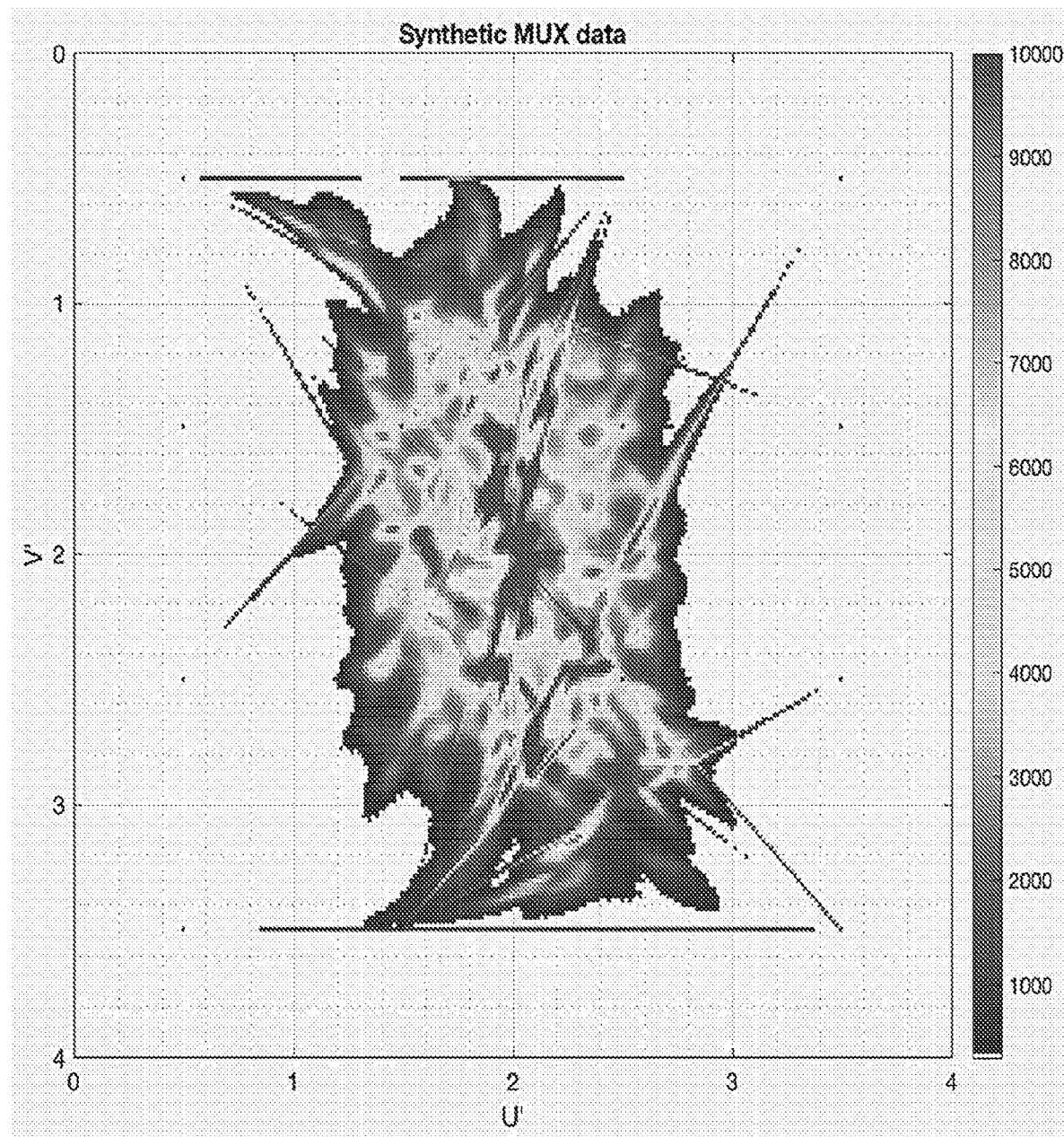
FIG. 9C and FIG. 9D illustrates a comparison between a synthetic multiplexed dataset and an actual multiplexed dataset multiplexed in accordance with aspects of the disclosure.
Figure 9D:
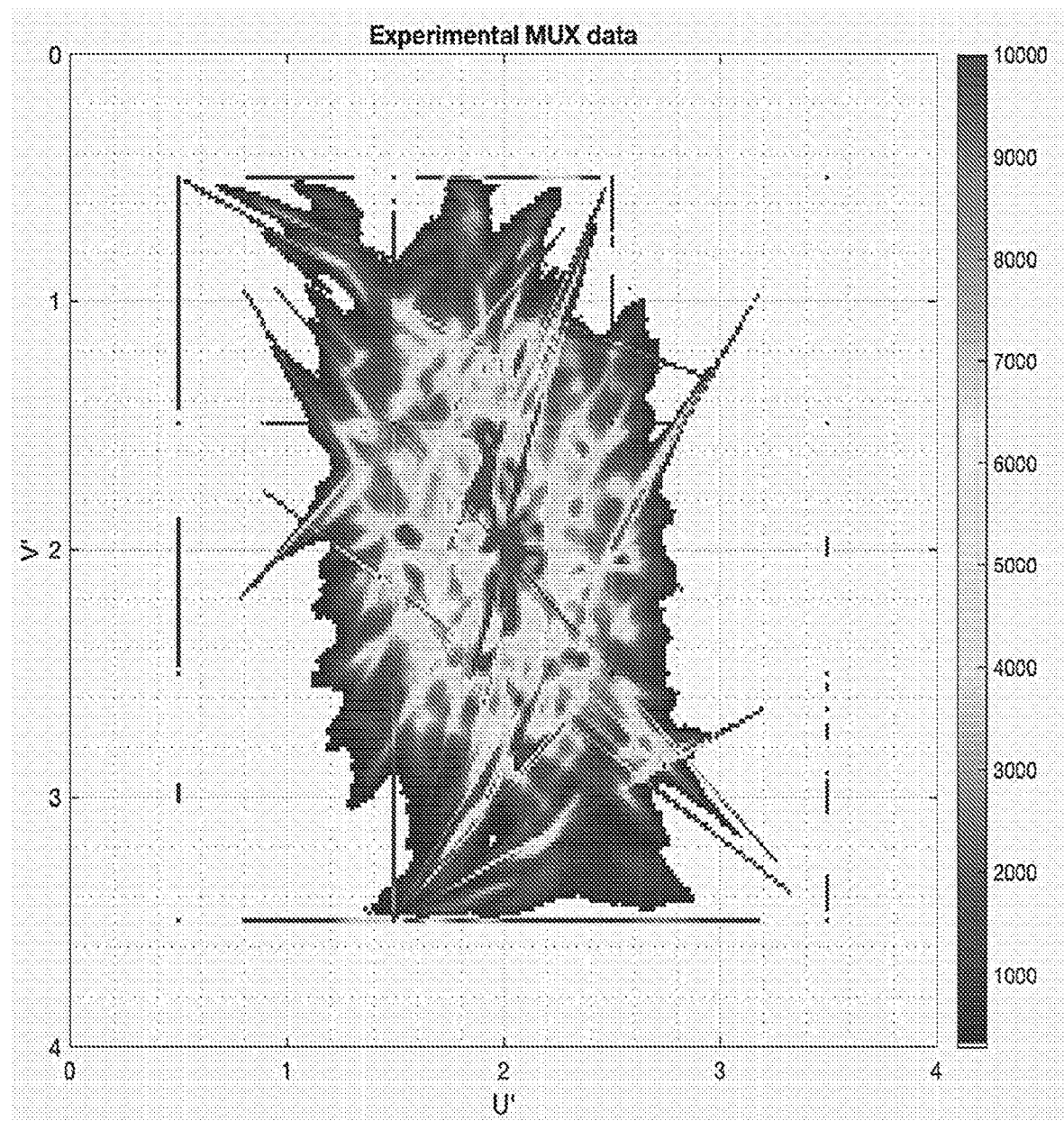

FIG. 9C shows an example of a synthetic dataset (computer-based multiplexed energy data) generated by added four sensor outputs in a similar manner described above (multiplexed) where a full resolution (e.g., 64) sensor outputs were read. FIG. 9D shows an example of multiplexed dataset generated from readout of multiplexed energy signals from a readout ASIC 405 where the readout ASIC 405 is connected to the sensor array 210 via the multiplexing scheme as described above. A comparison of FIG. 9C and FIG. 9D show that the datasets are very similar but slightly different due to imperfect model convergence. FIG. 9C and FIG. 9D show the mapping in U' and V' space which is done to show the channels in a square.

Figures 10A, 10B:
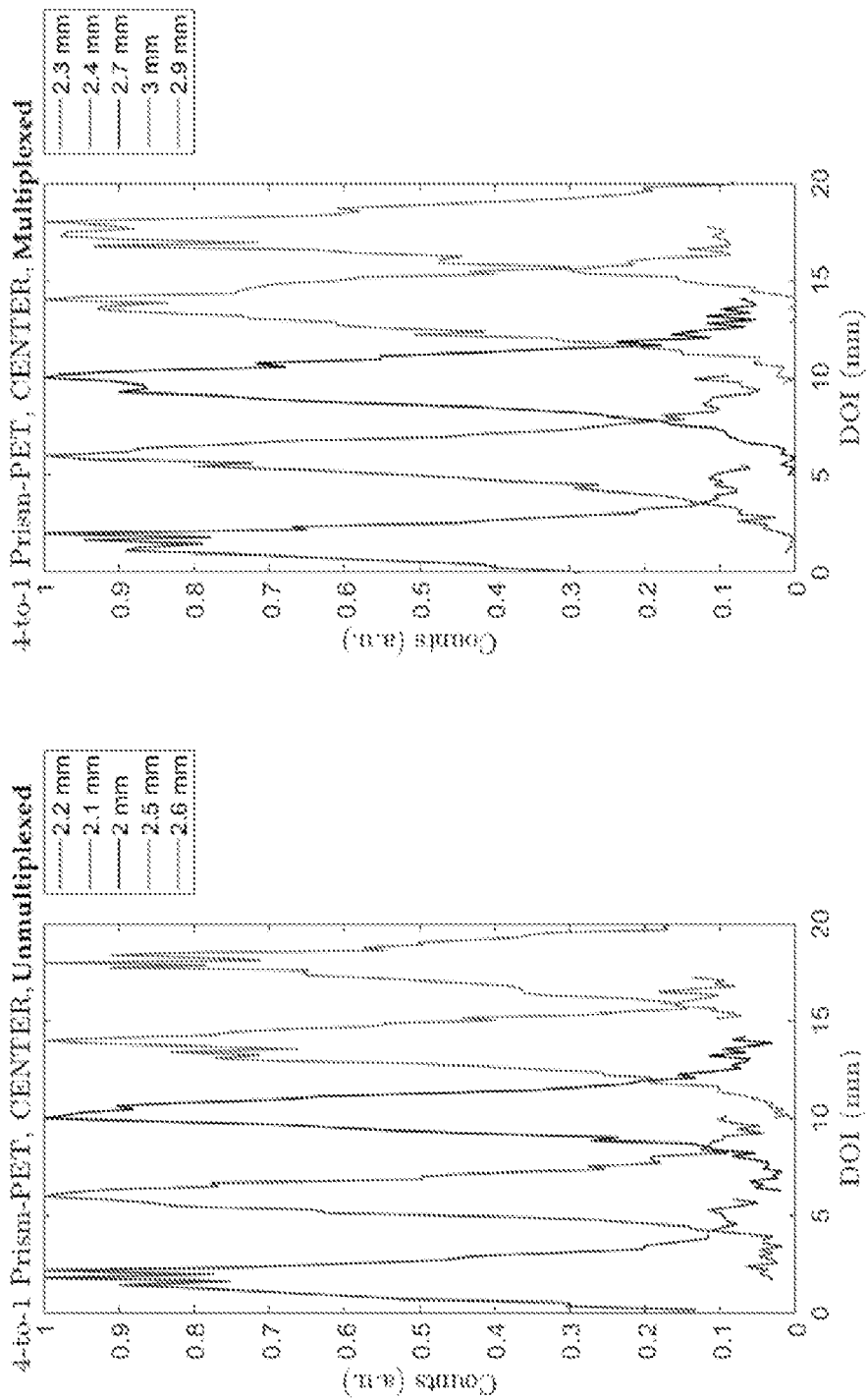
FIG. 10A and FIG. 10B illustrate a comparison between DOI resolution in a related particle detection system verses the DOI resolution of a particle detection system in accordance with aspect of the disclosure for a 4-to-1 scintillator module to optical sensor coupling.

FIG. 10A and FIG. 10B illustrate a comparison between DOI resolution in a related particle detection system verses the DOI resolution of a particle detection system in accordance with aspect of the disclosure for a 4-to-1 scintillator module to optical sensor coupling for the five different depths (2, 6, 10, 14 and 18 mm). The comparison is for a center optical sensor in the optical sensor array and another center optical sensor in the optical sensor array. In FIG. 10A, a "classical" calculation approach was used. In the classical approach, equation 1 was calculated using the highest energy signal (Pmax for the optical sensor or pixel basis) and the P was calculated from the sum of each energy channel (not multiplexed and therefore all 64 energy channel values were added). In FIG. 10B, the DOI was directly calculated by the computer-based multiplexed energy signals. For example, Pmax was determined as the highest signal from the 16 computer-based multiplexed energy signals and P was determined from the sum of the highest four signals from the 16 computer-based multiplexed energy signals.

The DOI estimation distribution were similar for the non-multiplexed data (FIG. 10A) and the multiplexed data (FIG. 10B). Average DOI resolution across all measured depths was 2.32 mm full-width at half-maximum (FWHM) for the non-multiplexed data (FIG. 10A) and 2.73 mm FWHM for the multiplexed data (FIG. 10B).

Figure 11A:
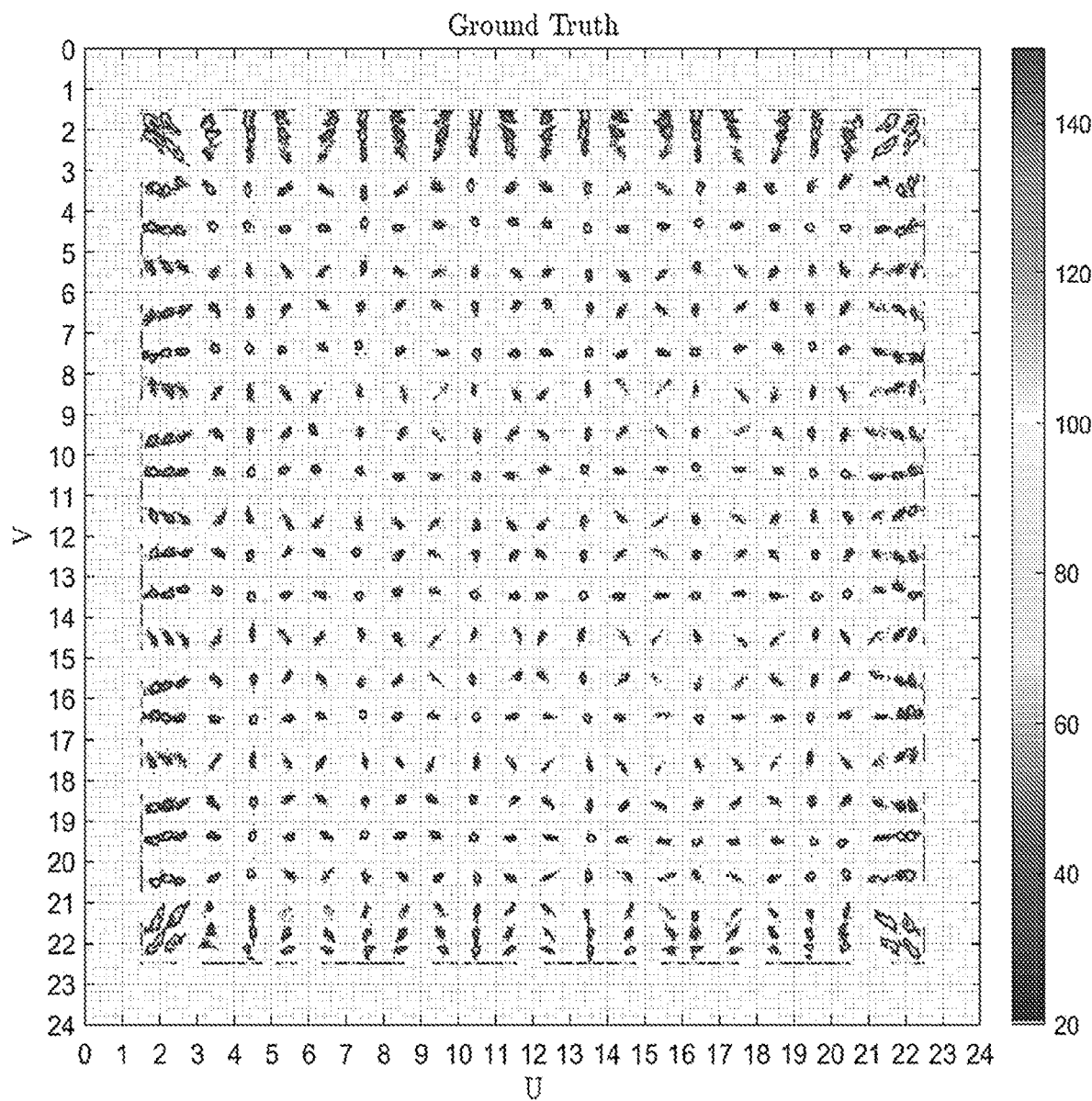
FIG. 11A and FIG. 11B illustrate a comparison between a ground truth and demultiplexing the multiplexed signals using the machine learning model in accordance with aspects of the disclosure for a 9-to-1 scintillator module to optical sensor coupling.
Figure 11B:
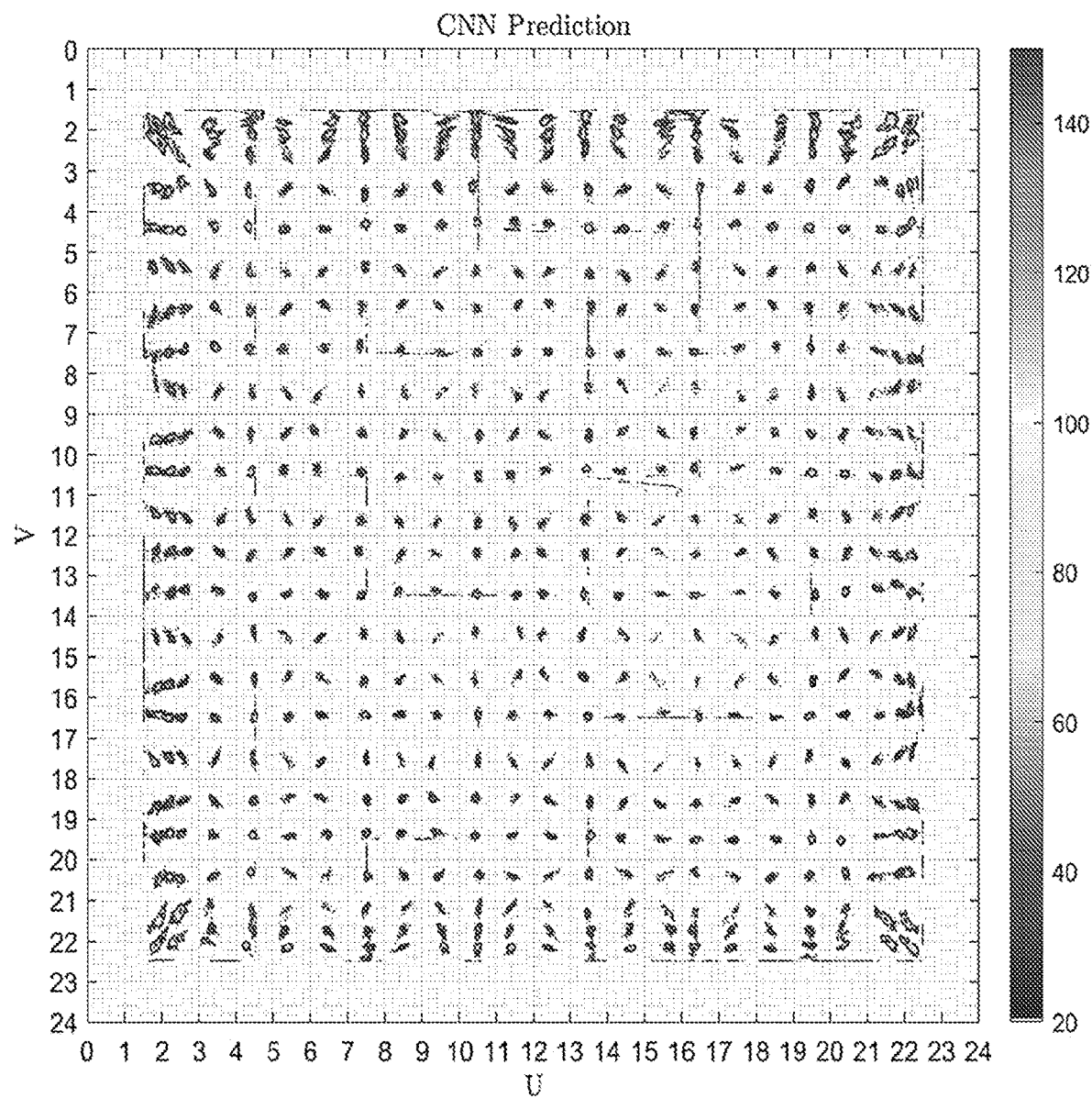

FIGS. 11A and 11B illustrate a qualitative comparison of the actual energy signals output from each of the plurality of optical sensors (without multiplexing) and predictions obtained from the trained/tested machine learning model on computer-based multiplexed energy signals using the multiplexing scheme as described herein (demultiplexed) from the 9-to-1 scintillator module to optical sensor coupling. Excellent scintillator module separation was achieved in the center and edge scintillator modules with comparable performance between the non-multiplexed data (FIG. 11A) and the multiplexed data (FIG. 11B).

Figures 12A, 12B:
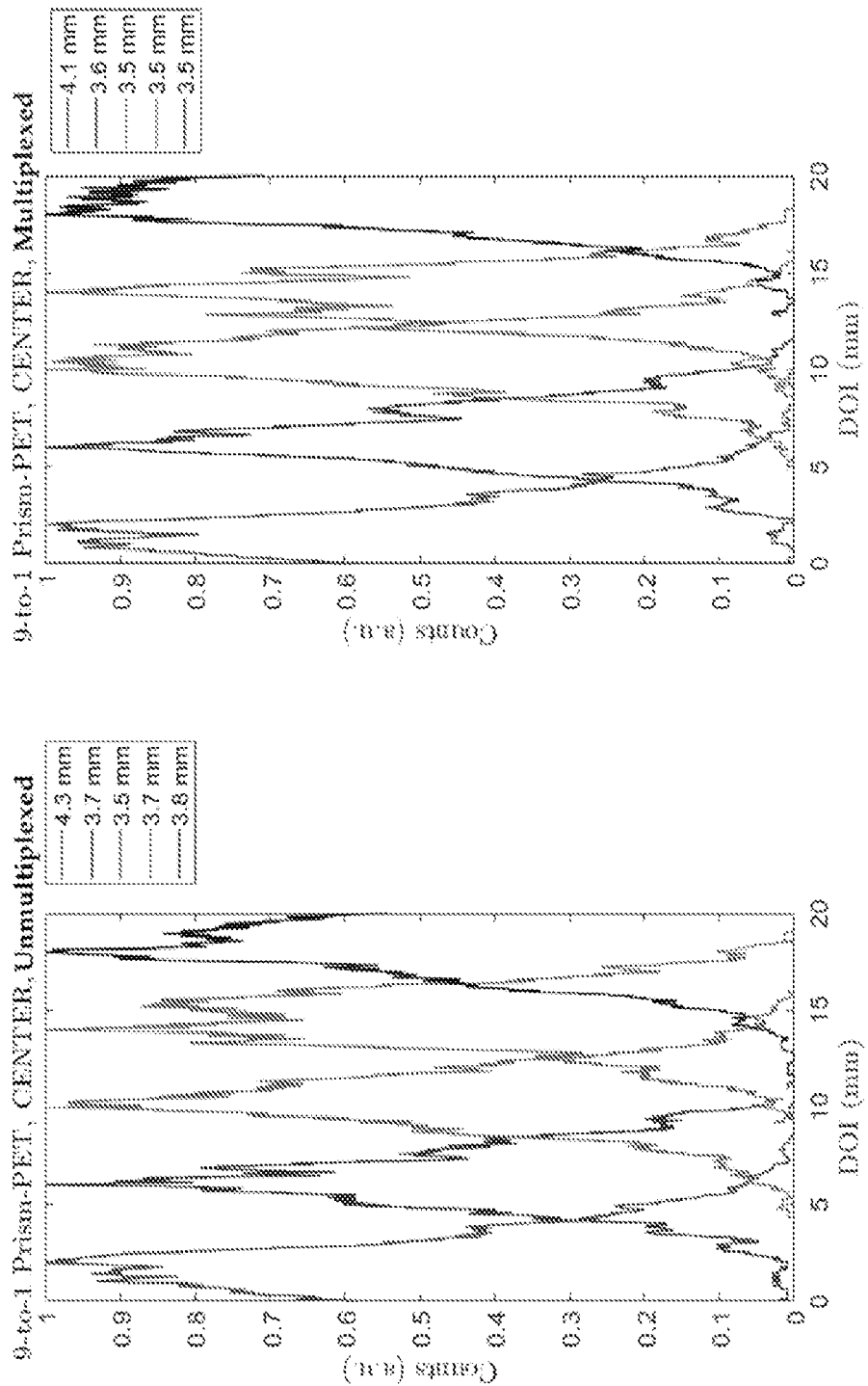
FIG. 12A and FIG. 12B illustrate a comparison between DOI resolution in a related particle detection system verses the DOI resolution of a particle detection system in accordance with aspect of the disclosure for a 9-to-1 scintillator module to optical sensor coupling.

FIG. 12A and FIG. 12B illustrate a comparison between DOI resolution in a related particle detection system verses the DOI resolution of a particle detection system in accordance with aspect of the disclosure for a 9-to-1 scintillator module to optical sensor coupling for the five different depths (2, 6, 10, 14 and 18 mm). The comparison is for a center optical sensor in the optical sensor array and another center optical sensor in the optical sensor array. In FIG. 12A, a "classical" calculation approach was used. In the classical approach, equation 1 was calculated using the highest energy signal (Pmax for the optical sensor or pixel basis) and the P was calculated from the sum of each energy channel (not multiplexed and therefore all 64 energy channel values were added). In FIG. 12B, the DOI was directly calculated by the computer-based multiplexed energy signals. For example, Pmax was determined as the highest signal from the 16 computer-based multiplexed energy signals and P was determined from the sum of the highest four signals from the 16 computer-based multiplexed energy signals.

The DOI estimation distribution were similar for the non-multiplexed data (FIG. 12A) and the multiplexed data (FIG. 12B). Average DOI resolution across all measured depths was 3.8 mm full-width at half-maximum (FWHM) for the non-multiplexed data (FIG. 12A) and 3.64 mm FWHM for the multiplexed data (FIG. 12B).

The percent error for CNN prediction with respect to energy-weighted average methods for x- and y-coordinates was 2.05% and 2.15%, respectively, for 4-to-1 scintillator module to optical sensor coupling, and 2.41% and 1.97% for 9-to-1 scintillator module to optical sensor coupling. The percent error for total detected energy per event for the multiplexed data following CNN prediction was 1.53% for 4-to-1 scintillator module to optical sensor coupling and 1.69% for 9-to-1 scintillator module to optical sensor coupling.

The above test demonstrates that any difference between the system's performance by using the described multiplexing scheme as described herein is minimal due to the deterministic light sharing which is a result of the segmented prismatoid light guide. It is noted that the observed difference may be a result of the experiment conditions such as using the 3 MBq Na-22 sodium point source (1 mm active diameter). The multiplexing results the data output from the optical sensor array into the readout ASIC and connections. Minimizing the size of the data files is especially critical as the field shifts toward DOI PET, which depending on the readout scheme and DOI resolution (which determines the number of DOI bins), may increase the effective number of Lines of Response (LORs) by more than 2 orders of magnitude.

As described above, using multiple timestamps per energy channel improves the CTR for the system. To demonstrate the improvement, events were simulated in software for two coincident detection modules. In the simulation, the energy channels were not multiplexed. However, since there is light sharing and since the above described multiplexing does not multiplex optical sensors associated with the same prismatoid segment, the CTR (and respective timing in each module) should not be impacted. Each detection module was simulated to have a 16×16 LYSO arrays, where each scintillator module was 1.5 mm×1.5 mm×20 mm. There was a 4-to-1 coupling. Each SiPM (pixel) was simulated to have the dimensions of 3.2 mm×3.2 mm. The segmented prismatoid light guide described herein was used in the simulation. As described herein, the segmented prismatoid light guides increase the light sharing ratios for all scintillator modules coupled to the same prismatoid segment, thus introducing a depth encoding signal. Reflective material between the scintillator modules was also included in the simulation.

The 511 keV gamma ray absorptions were simulated as spherical light sources (0.1 mm diameter) with emission equal to the light yield of LYSO (~27,000 photons/MeV). Events were distributed based on Beer-Lambert law for photoelectric absorption in lutetium with respect to depth in the scintillators. Energy deposition curves as a function of time were generated for each absorption and convolved with the photoresponse of silicon photomultipliers with various single photon time resolutions (SPTR=10, 50 and 100 ps). The overall photopeak energy resolution was simulated to be 10%.

Timestamps were generated based on three trigger thresholds corresponding to a number of photons collected on the readout side (n=5, 10 and 50 photons) (examples of the voltage threshold described herein). A uniformly distributed timing offset ($t_{off}$=0-1667 ps (also referred to herein as TOF), which corresponds to a positional offset from (0-50 cm) was added to the timestamps from one of the two crystals for each coincidence pair. This was to simulate actual movement of the radiation source between the coincident detection modules.

While ground truth DOI is known in the simulation, the DOI parameter used for CNN training and testing was calculated separately using an energy-weighted average method. 3 separate simulations were performed: 2 coincident center crystals, 2 coincident edge crystals and 2 coincident corner crystals to independently characterize the timing performance in these 3 regions. 60,000 events were simulated in each of the 3 cases for a total of 30,000 coincidence pairs per simulation.

A batch size of 20 and 100 epochs were used for training. The difference between ground truth and CNN output $t_{off}$ values for each coincidence pair in the test dataset were calculated and the standard deviation of the error distribution to characterize the CTR of the CNN was calculated. CNN performance precision was characterized by running each training case 10 times, while reshuffling and redistributing data between training and testing datasets, and calculating the mean and standard deviation of the CTR values for each case.

The above-described CNN (FIG. 17) was used to predict the TOF (Toff). Six different input layers were used: 1 timestamp, 2 timestamps, 1 timestamp with DOI correction, 2 timestamps with DOI correction, three timestamps and three timestamps with DOI correction. FIG. 18 illustrates a table of the results. The table is sorted by the SPTR 100, 50 and 10, respectively. For each SPTR, the six different input layers are shown. As can be seen, the CTR improves when two or three timestamps are used verses one timestamp. For example, for the SPTR of 100, when one timestamp is used for a SiPM associated with a center prismatoid 162, the CTR is 195 (SD of 2.3), however when two timestamps are used the CTR is 136 (SD of 1.1) and when three timestamps are used the CTR is even lower at 124 (SD of 1.5). A similar improvement is shown for the other prismatoid designs (corner and edge). The improvement is even more noticeable when DOI correction is used (depth encoding YES). As can be seen in FIG. 18, the best results (highlight) are for three timestamps and Depth encoding YES. FIG. 18 shows a comparison with "a classical CTR". Classical CTR did not use any machine learning and calculated TOF using the difference in the detected timestamps (NO depth encoding). With depth encoding a linear regression between TOF and DOI was performed to determine the contribution of DOI to TOF, and that contribution is subtracted out to obtain for accurate TOF estimates.

The terms "segment" and "prismatoid segment" has been used interchangeably herein. The terms "segmented light guide", "prismatoid light guide", "segmented prismatoid light guide" also have been used interchangeably herein.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one aspect", "certain aspects", "some aspects" or "an aspect", indicate that the aspect(s) described may include a particular feature or characteristic, but every aspect may not necessarily include the particular feature, structure, or characteristic. Moreover, such phrases are not necessarily referring to the same aspect. Further, when a particular feature, structure, or characteristic is described in connection with an aspect, it is submitted that it is within the knowledge of one skilled in the art to affect such feature, structure, or characteristic in connection with other aspects whether or not explicitly described. For purposes of the description hereinafter, the terms "upper", "lower", "right", "left", "vertical", "horizontal", "top", "bottom", and derivatives thereof shall relate to a device relative to a floor and/or as it is oriented in the figures.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

As used herein, the term "processor" may include a single core processor, a multi-core processor, multiple processors located in a single device, or multiple processors in wired or wireless communication with each other and distributed over a network of devices, the Internet, or the cloud. Accordingly, as used herein, functions, features or instructions performed or configured to be performed by a "processor", may include the performance of the functions, features or instructions by a single core processor, may include performance of the functions, features or instructions collectively or collaboratively by multiple cores of a multi-core processor, or may include performance of the functions, features or instructions collectively or collaboratively by multiple processors, where each processor or core is not required to perform every function, feature or instruction individually. For example, a single FPGA may be used or multiple FPGAs may be used to achieve the functions, features or instructions described herein. For example, multiple processors may allow load balancing. In a further example, a server (also known as remote, or cloud) processor may accomplish some or all functionality on behalf of a client processor. The term "processor" also includes one or more ASICs as described herein.

As used herein, the term "processor" may be replaced with the term "circuit". The term "processor" may refer to, be part of, or include processor hardware (shared, dedicated, or group) that executes code and memory hardware (shared, dedicated, or group) that stores code executed by the processor.

Further, in some aspect of the disclosure, a non-transitory computer-readable storage medium comprising electronically readable control information stored thereon, configured in such that when the storage medium is used in a processor, aspects of the functionality described herein is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term memory hardware is a subset of the term computer-readable medium.

The described aspects and examples of the present disclosure are intended to be illustrative rather than restrictive, and are not intended to represent every aspect or example of the present disclosure. While the fundamental novel features of the disclosure as applied to various specific aspects thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or aspects of the disclosure may be incorporated in any other disclosed or described or suggested form or aspects as a general matter of design choice. Further, various modifications and variations can be made without departing from the spirit or scope of the disclosure as set forth in the following claims both literally and in equivalents recognized in law.

What is claimed is:

1. A particle detection system comprising:
   an optical sensor array comprising a first plurality of optical sensors, each optical sensor in the array corresponding to a pixel;
   a scintillator array comprising a second plurality of scintillator modules, the second plurality of scintillator modules being greater than the first plurality of optical sensors, where multiple scintillator modules are in contact with a respective optical sensor at a first end of the respective scintillator modules; and
   a segmented light guide comprising a plurality of prismatoid segments, the segmented light guide is in contact with a second end of the second plurality of scintillator modules, each prismatoid segment being in contact with scintillator modules that are in contact with at least two different optical sensors, the at least two different optical sensors being adjacent optical sensors, and
   where each prismatoid segment is configured to redirect particles between scintillator modules in contact with the respective prismatoid segment;
   wherein there are a third plurality of energy readout channels, where multiple optical sensors are connected to an energy readout channel, respectively, such that optical sensors associated with the same prismatoid segments are not connected to the same energy readout channel and wherein each energy readout channel has at least two timestamps associated therewith.

2. The particle detection system of claim 1, wherein the at least two timestamps is three timestamps.

3. The particle detection system of claim 1, further comprising at least two comparators connected to the multiple optical sensors for the same energy readout channel, for each energy readout channel, each of the at least two comparators having a different threshold.

4. The particle detection system of claim 3, wherein the at least two comparators are connected to each respective anode of the multiple optical sensors.

5. The particle detection system of claim 3, wherein the at least two comparators are connected to each respective cathode of the multiple optical sensors.

6. The particle detection system of claim 3, wherein the third plurality of energy readout channels and the at least two comparators are connected to different terminals of the optical sensors.

7. The particle detection system of claim 1, wherein the number of the multiple optical sensors connected to the same energy readout channel is 4.

8. The particle detection system of claim 1, wherein there is a four-to-one scintillator module to optical sensor coupling.

9. The particle detection system of claim 1, wherein there is a nine-to-one scintillator module to optical sensor coupling.

10. The particle detection system of claim 1, further comprising a first processor configured to bias the first plurality of optical sensors during readout and receive output via the third plurality of energy readout channels and the at least two timestamps associated with each energy readout channel.

11. The particle detection system of claim 10, further comprising a second processor in communication with the first processor, wherein the second processor is configured to determine a timing parameter for an event based on the received at least two timestamps.

12. The particle detection system of claim 11, wherein the timing parameter is based on a combination of the at least two timestamps.

13. The particle detection system of claim 11, wherein the second processor is configured to determine a time of flight (TOF) between coincident detection modules based on the timing parameter.

14. The particle detection system of claim 13, wherein the second processor is configured to determine the TOF using a machine learning model having input the received at least two timestamps from the coincident detection modules.

15. The particle detection system of claim 11, wherein the second processor is further configured to determine at least one of a primary interaction pixel, a primary interaction scintillator module or a depth of interaction for the event.

16. The particle detection system of claim 15, wherein the second processor is configured to select the at least two timestamps associated with the determined primary interaction pixel to determine the timing parameter.

17. The particle detection system of claim 11, wherein the timing parameter is based at least on a fastest timestamp.

18. The particle detection system of claim 11, wherein the timing parameter is based on a linear regression analysis of the received at least two timestamps.

19. The particle detection system of claim 1, wherein the first plurality of optical sensors is arranged in rows and columns and wherein adjacent optical sensors in a row are connected to different energy readout channels and adjacent optical sensors in a column are connected to different energy readout channels.

* * * * *